US009381346B2

(12) United States Patent
Lee et al.

(10) Patent No.: US 9,381,346 B2
(45) Date of Patent: Jul. 5, 2016

(54) TREATMENT OF NEUROLOGICAL DISORDERS VIA ELECTRICAL STIMULATION, AND METHODS RELATED THERETO

(75) Inventors: Harry Lee, Boston, MA (US); Allan Foreman, Epping, NH (US); Wolfgang Daum, Groton, MA (US); Richard Cohen, Chestnut Hill, MA (US); Jean Gotman, Westmount (CA); Andrew James Cole, Lincoln, MA (US)

(73) Assignee: Precisis US, Inc., Groton, MA (US)

( * ) Notice: Subject to any disclaimer, the term of this patent is extended or adjusted under 35 U.S.C. 154(b) by 614 days.

(21) Appl. No.: 12/319,158

(22) Filed: Jan. 2, 2009

(65) Prior Publication Data

US 2011/0137381 A1      Jun. 9, 2011

Related U.S. Application Data

(63) Continuation of application No. PCT/US2007/015446, filed on Jul. 5, 2007.

(60) Provisional application No. 60/818,553, filed on Jul. 5, 2006, provisional application No. 60/848,481, filed on Sep. 29, 2006.

(51) Int. Cl.
*A61N 1/05* (2006.01)
*A61N 1/36* (2006.01)

(52) U.S. Cl.
CPC ............ *A61N 1/0529* (2013.01); *A61N 1/0531* (2013.01); *A61N 1/36017* (2013.01); *A61N 1/36025* (2013.01); *A61N 1/36082* (2013.01)

(58) Field of Classification Search
USPC .................. 607/45, 67, 139, 148; 600/393, 600/544–545
See application file for complete search history.

(56) References Cited

U.S. PATENT DOCUMENTS 4,936,306 A    6/1990    Doty
5,111,812 A    5/1992    Swanson et al.
(Continued)

FOREIGN PATENT DOCUMENTS

CA        1219642 A       3/1987
JP     2001-271203 A     10/2001
(Continued)

OTHER PUBLICATIONS

Fasiuddin, M., "Depth Perception Using Concentric Ring Electrodes," Master's Thesis presented to the College of Engineering and Science at Louisiana Tech University, 2005.
(Continued)

*Primary Examiner* — Paula J Stice
(74) *Attorney, Agent, or Firm* — Kristina Bieker-Brady; Clark & Elbing LLP

(57) ABSTRACT

The present invention features a medical device and methods for the prevention and/or treatment of neurological disorders via electrical stimulation. These device are minimally or non-invasive and are capable of detection of a neurological disorder and its subsequent prevention or treatment. Specifically, seizure control is among the targeted therapeutic areas. Components of the device include control electronics and electrodes; the latter are targeting electrodes located entirely outside the skull and can be constructed from ring type structures or virtually connected disc type arrays. Other sub-systems included in the medical device are a control system, a battery unit, and wires connecting these and other sub-systems.

14 Claims, 24 Drawing Sheets

(56) References Cited

U.S. PATENT DOCUMENTS

| | | | |
|---|---|---|---|
| 5,792,186 | A | 8/1998 | Rise |
| 5,873,898 | A | 2/1999 | Hemming et al. |
| 6,016,449 | A | 1/2000 | Fischell et al. |
| 7,006,859 | B1 | 2/2006 | Osorio et al. |
| 7,010,351 | B2 | 3/2006 | Firlik et al. |
| 7,101,351 | B2 | 9/2006 | Crawford et al. |
| 7,221,981 | B2 | 5/2007 | Gliner |
| 7,305,268 | B2 | 12/2007 | Gliner et al. |
| 8,190,248 | B2 | 5/2012 | Besio et al. |
| 8,204,572 | B1 | 6/2012 | Lang et al. |
| 2002/0072770 | A1 | 6/2002 | Pless |
| 2003/0050673 | A1 | 3/2003 | Yamazaki et al. |
| 2003/0158587 | A1 | 8/2003 | Esteller et al. |
| 2003/0187490 | A1 | 10/2003 | Gliner |
| 2004/0102828 | A1 | 5/2004 | Lowry et al. |
| 2004/0153129 | A1 | 8/2004 | Pless et al. |
| 2004/0158298 | A1 | 8/2004 | Gliner et al. |
| 2004/0199237 | A1 | 10/2004 | Mills et al. |

FOREIGN PATENT DOCUMENTS

| | | |
|---|---|---|
| WO | WO 01/51122 | 7/2001 |
| WO | WO 02/072194 | 9/2002 |
| WO | WO 03/089057 | 10/2003 |
| WO | WO-03/089057 A1 | 10/2003 |

OTHER PUBLICATIONS

International Search Report from PCT/US2007/015446, dated Jul. 25, 2009.

European Patent Office Communication and Extended European Search Report for EP 05808963.2-2305, dated May 11, 2010.

Translation of "Notice of Reasons for Rejection" for Patent Application No. JP 2007-536997, dated Jul. 19, 2011.

Extended European Search Report for European Patent Application No. 05808963.2, dated May 11, 2010 (6 pages).

International Preliminary Report on Patentability for International Patent Application No. PCT/US2005/037246, dated May 30, 2007 (7 pages).

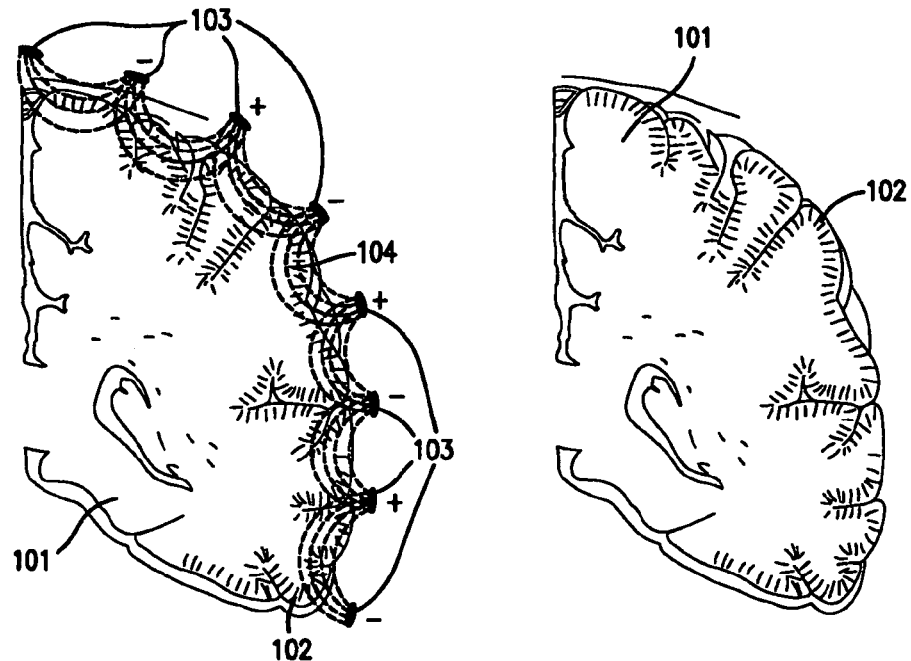
FIG. 1A  FIG. 1B
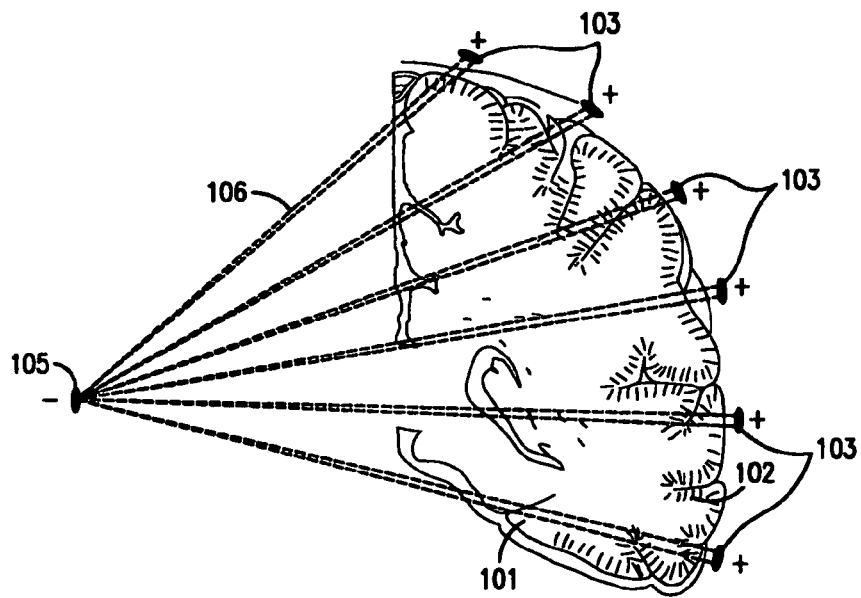
FIG. 1C

RIGHT

LEFT                    RIGHT

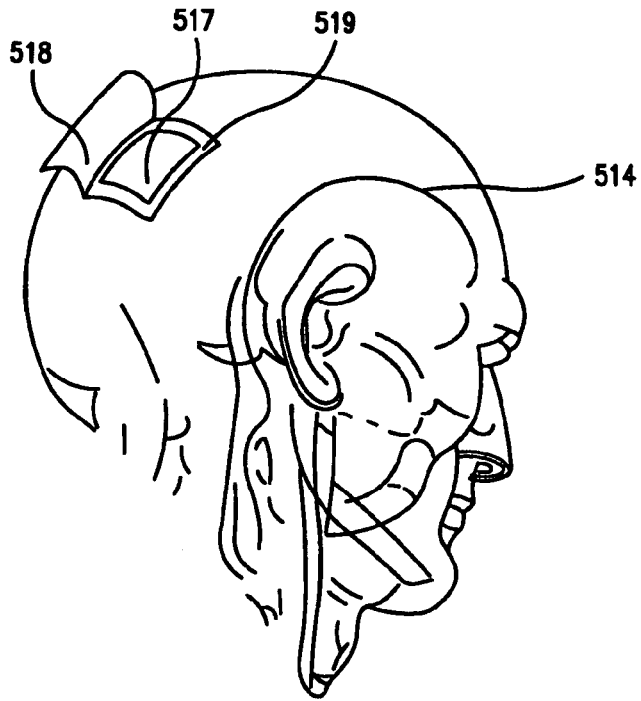
FIG. 5A1
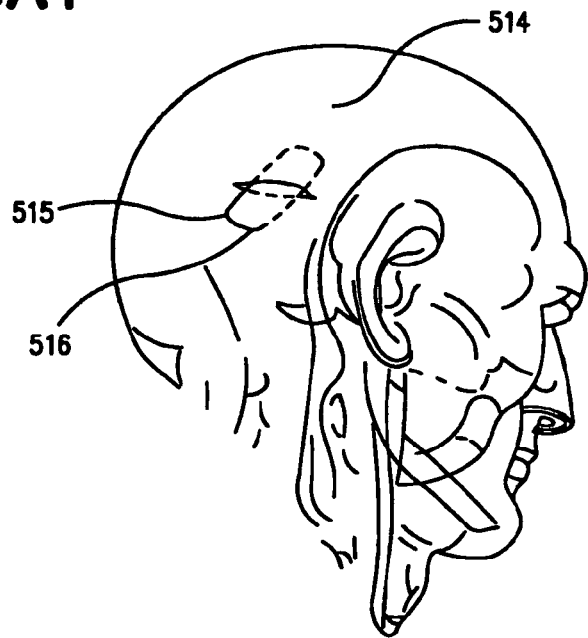
FIG. 5A2

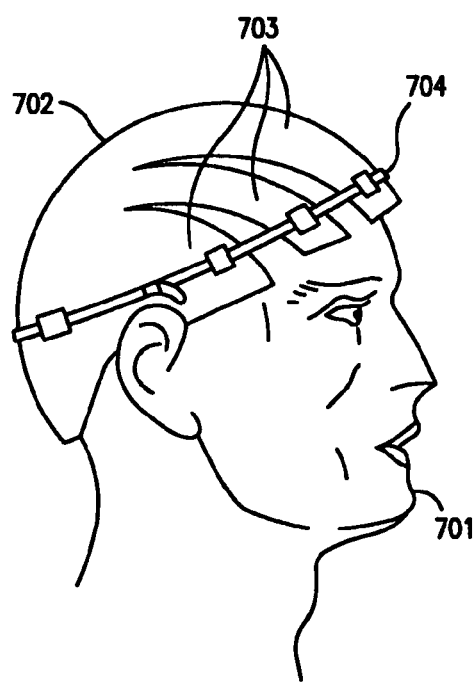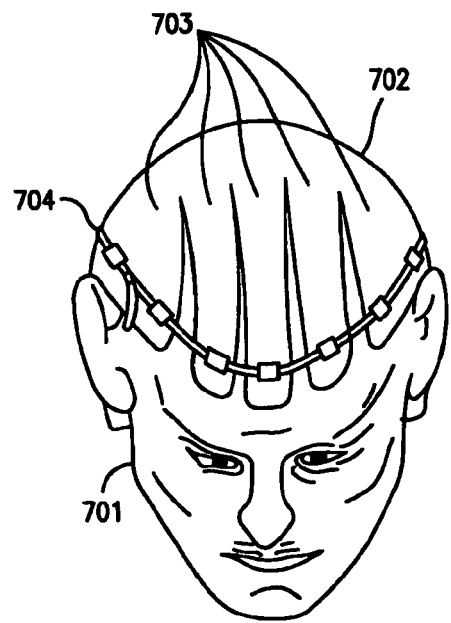
FIG. 7A  FIG. 7B

TREATMENT OF NEUROLOGICAL DISORDERS VIA ELECTRICAL STIMULATION, AND METHODS RELATED THERETO

CROSS REFERENCE TO RELATED APPLICATIONS

This is a non-provisional application claiming the benefit of and priority to Provisional Patent Application having Ser. No. 60/818,553 filed on Jul. 5, 2006, and to Provisional Patent Application having Ser. No. 60/848,481 filed on Sep. 29, 2006, both of which are incorporated herein by reference. This application claims priority from PCT/US2007/015446 as filed Jul. 5, 2007.

TECHNICAL FIELD

The present invention relates generally to medical devices, more specifically, to medical devices for the treatment of neurological disorders via electrical stimulation, and methods related thereto.

BACKGROUND

Electrical stimulation of neural or nervous tissue—neurostimulation—is a well established procedure for the treatment of various neurological disorders. Neurostimulation has been successfully applied to treat diseases, such as epilepsy, depression, Parkinson's disease, migraine, and for stroke rehabilitation. However, today's neurostimulation techniques have a lot of difficulties. In Vagus Nerve Stimulation (VNS) electrodes are implanted around the vagus nerve, which carries the signal rather systemically but not targeted into the brain. The VNS technique has a rather low efficacy in successfully treating epilepsy or depression. In Deep Brain Stimulation (DBS) and Responsive Neuro Stimulation (RNS), electrodes are implanted within the cranium having direct contact with the brain. The invasiveness of both techniques is a large barrier for using these techniques. In Transcranial Magnetic Stimulation (TMS), alternating magnetic fields are utilized to induce eddy currents in parts of the brain where they cause electrical stimulation. However, TMS requires rather large equipment and can not be built into a portable device that a patient can carry for the treatment of epilepsy or other chronic diseases. In Electroconvulsive Therapy (ECT), patients receive, under anesthesia, rather large electrical shocks. ECT can not be made as a portable technique to treat chronic diseases.

Intracranial stimulation in which the stimulating electrodes are located directly at the disease site appears to be the most promising stimulation treatment for chronic illnesses, such as epilepsy, Parkinson's, depression, and others. However, intracranial stimulation techniques are very invasive.

Concentric ring electrodes capable of delivering stimulation to defined brain areas have been disclosed in the art (e.g., WO/2006/04479), however, for diseases such as epilepsy, all current techniques can only be used if the foci of the seizure(s) are known and static, meaning the foci do not move away from the location of the electrodes or become larger beyond the region of the location of the electrodes. A partial epileptic seizure can transform into a generalized seizure when the focus is enlarged and spreads out to the size of the entire brain. Currently, there is no neurostimulation technique available that stimulates specific targeted brain tissue areas, is adaptable to moving or dynamically shape changing foci, and is less invasive.

SUMMARY OF THE INVENTION

As discussed above, currently available intracranial stimulation techniques fail to provide a safe, effective and less invasive means of treating neurological disorders, particularly involving brain tissue. It is, therefore, an object of the present invention to provide a safe, effective and less invasive targeted brain stimulation technique that does not require intracranial electrodes and is capable of following moving or dynamically shape changing targets, such as epileptic seizure foci.

It is also an object of the present invention to provide a permanent implant for the treatment of chronic epilepsy.

Further, recent research has demonstrated that direct current stimulation can prevent seizure activity. It is, therefore, an object of the invention to combine a preventive stimulation approach with acute responsive stimulation for epilepsy.

It is another object of the present invention to provide various possible and optimal configurations of the stimulating or sensing electrodes.

It is a further object of the present invention to provide devices and methods that can be useful for acute or chronic treatment or suppression of neurological disorders, which may be diseases, disorders or conditions of the brain and nervous system or psychiatric disorders or conditions.

The present invention pertains to medical devices for the prevention, and/or treatment of neurological disorders, based on electrical stimulation. In one embodiment a system is provided for delivering an electrical stimulation into the brain of a patient. The system includes at least one electrode adapted for placement between a patient's scalp and cranium to monitor electrical activity in the patient's brain; and a control module operatively coupled to the at least one electrode. The control module includes a detection sub-system for detecting abnormal electrical activity within the brain and a responsive analysis sub-system for analyzing the abnormal electrical activity within the brain. A responsive stimulation sub-system is operatively controlled by the control module to deliver an electrical responsive stimulation into the patient's brain in response to the responsive analysis sub-system. A preventive stimulation sub-system is operatively controlled by the control module to deliver an electrical preventive stimulation into the patient's brain independent of the responsive analysis sub-system, to alter the onset of abnormal electrical activity within the patient's brain.

The present invention pertains to a system for the treatment of neurological disorder in a patient. The system includes a plurality of electrodes of any type, arranged in an array adapted for placement outside the brain of a patient to sense the patient's electrical brain activity, a power supply, and a control module operatively coupled to the power supply. The control module includes a switching sub-system operatively coupling the control module to the plurality of electrodes. The switching module selects electrodes among the plurality of electrodes so as to switch selected electrodes between first and second patterns about the patient's brain without altering the placement of the plurality of electrodes. The control module further includes an analysis sub-system to analyze the electrical activity sensed by the selected electrodes.

The present invention also pertains to methods for the detection, prevention, and/or treatment of neurological disorders or symptoms. In one embodiment, the method involves the steps of positioning at least one electrode outside the patient's brain, detecting electrical activity within the brain consistent with a neurological event, and analyzing the neurological event to determine whether the neurological event is abnormal. Also included is the step of delivering an electrical responsive stimulation into the patient's brain through the at least one electrode in response to an abnormal neurological event and delivering an electrical preventive stimulation into the patient's brain, independent of analyzing the neurological event, so as to alter the onset of the neurological event within the patient's brain.

In another embodiment, the method involves the steps of positioning a plurality of electrodes of any type in an array, outside the patient's brain, and using the electrodes for detecting electrical activity within the brain. A power supply is operatively coupled to the control module, and the control module is coupled to the plurality of electrodes through a switching sub-system, employed for selecting electrodes among the plurality of electrodes, and switching the selected electrodes between first and second preselected patterns about the patient's brain, without altering the placement of the plurality of electrodes. The method also includes the step of analyzing the electrical activity sensed by the selected electrodes.

As will be explained herein, the present invention is, in part, directed to substrate modification, involving altering the electrical properties of the brain by preventive chronic stimulation not in response to recorded brain electrical activity, as well as stimulation of the brain in response to observed brain electrical activity.

The above summary of the present invention is not intended to describe each illustrated embodiment or every implementation of the present invention. The figures and the detailed description which follow particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1A-C schematically illustrate coronal sections of one hemisphere of the human brain and electrodes, according to an embodiment of the present invention (Skin, bone, spinal fluid and other anatomical structures are not shown to concentrate the reader's eyes on the essential inventive parts);

FIGS. 5A1 and 5A2 schematically illustrate methods for implanting targeted electrodes (dashed lines present structures covered by skin), according to an embodiment of the present invention;

FIG. 7 schematically illustrates an acute seizure control helmet or cap as used on the head of a patient, according to an embodiment of the present invention;

Figure 2A:
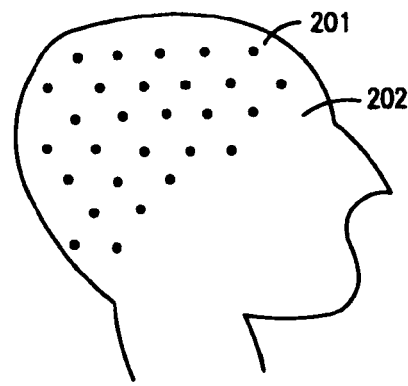
FIG. 2A-L schematically illustrate various examples of the geometric forms and arrangements of stimulating electrodes and possible electrical phasing patterns on a mammalian head, according to an embodiment of the present invention.

Dimensions provided in the figures, if any, are for illustrative purpose only; the dimensions of the actual device(s) may be different. Targeting electrodes that are sometimes shown and discussed as solid ring type electrodes can always be replaced with targeting electrodes constructed from disc or point type electrodes in an array of discrete disc or point type electrodes. Although electrodes are shown in two dimensions, in reality they are curved according to the three-dimensional surface geometry of the human head. Wiring to and from the electrodes may not be shown on the drawings for simplicity purposes.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF EXEMPLARY EMBODIMENTS

The present invention pertains to medical devices for the prevention and/or treatment of various neurological disorders, based on electrical stimulation. The present invention also pertains to methods for preventing and/or treating neurological disorders utilizing such devices. These methods may also involve the detecting or sensing or neurological disorders prior to or during preventing or treating.

DEFINITIONS

The term "targeting electrodes", as used herein, refers to the geometric configuration of discrete type or ring type electrodes located outside the cranium and capable of delivering electrical stimulation to defined localized areas of the brain. The discrete or ring type electrodes can be of any shape, and can be symmetrically or unsymmetrically configured. Targeting electrodes can be constructed from arrays of discrete disc electrodes.

The term "concentric", as used herein, refers to electrode elements wherein larger elements surround smaller elements. In a preferred embodiment, conductive elements are configured as rings having consecutively increasing radius that surround a central conductive disc. In other embodiments, the conductive elements that surround the central electrode element may be square, rectangle, ellipse, or polygon comprising any number of sides. The conductive elements may also be irregularly shaped.

The term "electrode", as used herein, refers to an electric conductor through which an electric current enters or leaves an electrolytic cell or other medium. An electrode performs the function of delivering or receiving an electric signal. If not otherwise specified, the term electrode is used in this functional meaning and does not refer to any shape or form. The term "electrodes", "array of electrodes" or "arrangement of electrodes" does not refer to any specific geometric arrangement of electrodes and is not limited to any of the arrangements shown herein.

The term "neurological disorder" or "neurological disorders", as used herein, refers to any disorder, disease, and/or syndrome due to or resulting from neurologic, psychiatric, psychological, and/or cerebrovascular symptomology or origin. The term "neurological disorder" or "neurological disorders", as used herein, also refers to diseases, disorder or condition of the brain and nervous system or psychiatric disorders or conditions. Neurological disorders include, but are not limited to Absence of the Septum Pellucidum, Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS—Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Patsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia—Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated, Myelopathy, Huntington's Disease, Hydranencephaly, Hydrocephalus, Hydrocephalus—Normal Pressure, Hydromyelia, Hyperactivity, Hypercortisolism, Hypersomnia, Hypertonia, Hypotonia,—Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus—Neurological, Sequelae, Lyme Disease—Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Myopathy—Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy—Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain—Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome.

The term "stimulation", as used herein, refers to an electrical signal or signals applied to the brain or nervous system via the scalp, skull, or to near brain tissue, or to the near nervous system tissue, or to skin surface, such as on the face, spine, peripheral extremities, or neck.

The term "epicranial", as used herein, refers to a location under, on top or within the scalp, subgaleal, subpericranial, or subscalp.

The term "treatment", as used herein, refers to acute or chronic treatment, healing, curing, or rehabilitating.

The abbreviation "EEG", as used herein, refers to Electroencephalogram.

In general, all electrodes as shown herein can be located anywhere in the brain, within or on top of specific brain structures, on top of specific nerve structures, outside the brain and touching or not touching the cortex, between the cortex and the cranium, between the brain and facial bones, within the cranium, outside the cranium but under the skin (subscalp, subgaleal, or subpericranial), within the skin, on top the skin, or within or on top of the hair. In some cases, it may be necessary to utilize electrical conductive paste to enhance the conductivity the between electrodes and the tissue. This paste is not always shown in the figures or referred to in the text in order not to deviate the reader from the essentials of the invention.

It is to be understood that the singular forms of "a", "an", and "the", as used herein and in the appended claims, include plural reference unless the context clearly dictates otherwise.

Device Components

The medical device of the present invention comprises various components, which include electrodes and control electronics.

Electrode Configuration

FIG. 1A illustrates a coronal section of one hemisphere of the human brain 101. The direction of the neurons at the outer surface—cortex—of the brain is indicated in the figure with dashes 102. It can be seen that the general directions of the neurons is perpendicular to the surface. The gray cellular mantle of the cortex is 1-4 mm thick and covers the entire surface of the cerebral hemisphere of mammals, and it is characterized by a laminar organization of cellular and fibrous components.

FIG. 1B illustrates array electrodes 103 that may be located non-invasively on top of the skin (not shown in the figure), located subgaleally (under the scalp) or subcranially, the electrodes 103 locally alternate in their polarity (plus and minus). Further, the polarity changes with the stimulation frequency and stimulation pulsing pattern. The resulting electrical field lines 104 penetrate the outer cortex, mainly parallel to the surface. Neurons, which are primarily stimulated by electrical fields that pass through them longitudinally and that happen to lay parallel to the surface of the brain, will become stimulated by this stimulation mode.

FIG. 1C illustrates array electrodes 103 on one hemisphere and array electrodes 105 on the other hemisphere of the head; and both array electrodes 103 and 105 are connected to the skin (not shown here). In this case, all electrodes of one hemisphere are of similar polarity (plus) and just one electrode of the other hemisphere is of the opposite polarity (minus), thus allowing the electrical field lines 106 to penetrate perpendicular to the outer cortex. Neurons, which are primarily stimulated by electrical fields that pass through them longitudinally and that happen to lay perpendicular to the surface of the brain, will become stimulated by this stimulation mode.

The array electrodes 103 and 105 are shown in FIG. 1 as dots for exemplary purposes, but they can comprise any shape, form or size. The dots can be cross-sections of dot-like, disk-like, stripe-like, curve-like, or ring-like structures. Any electro-conductive paste lowering the electrical impedance of the contact between the electrodes and the skin and/or through the hair is not shown in the figure.

In one embodiment of the present invention, at any moment, all electrodes on the one side of the hemisphere comprise the opposite polarity from one electrode on the other side, while the remaining electrodes in this hemisphere are neutral.

In one embodiment of the present invention, at any moment, all electrodes on the one side of the hemisphere comprise the opposite polarity than all electrodes on the other side.

In one embodiment of the present invention, at any moment, any one or more groups of electrodes on the one side of the hemisphere comprise the opposite polarity from any one or more groups of electrodes on the other side.

In one embodiment of the present invention, at any moment, any groups of electrodes can be polarized opposite to any other groups of electrodes.

In one embodiment of the present invention, different groups of electrodes are polarized opposite to different other groups of electrodes in various equal or varying sequences.

Electrode Forms and Arrangements

FIG. 2A-L illustrate various electrode forms, shapes, and arrangements, as well as examples of charging these electrodes in any combination. 25

FIG. 2A illustrates an array or lattice of dot-like, disk-like or single- or multiring-like electrodes 201 on a mammalian head 202. The shape of the disk-like or single- or multi-ring-like electrodes can be circular, oval, irregular rounded, regular polygonal (equally angled triangle, square, pentagon, etc.), irregular polygonal, or any combination hereof. The arrangement of the electrodes 201 can be a symmetric lattice comprising any one or any combination of the five two-dimensional lattice types, mathematically wallpaper groups, or irregular. The five two-dimensional lattices are the rhombic-, hexagonal-, square-, rectangular-, or parallelogrammic lattice.

Figure 2B:
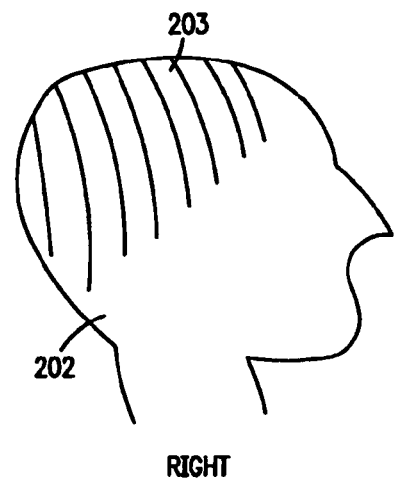

FIG. 2B illustrates an array of lattice of stripe-like electrodes 203 on the mammalian head 202. These electrodes can be of equal or irregular length or width, equally or irregularly spaced, in parallel or non parallel, straight or curved.

Figure 2C:
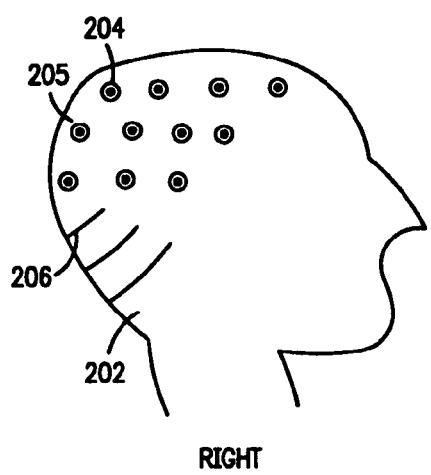

FIG. 2C illustrates an array or lattice of a combination of different types and forms of electrodes on the mammalian head 202. In this particular illustration, a group of electrodes comprising a center disc with one outer ring 204, a group of circular disc-type electrodes 205 and stripe-type electrodes 206 are shown. Any other combination of groups of symmetric or irregular lattices may also be suitable for use herein.

Figure 2D:
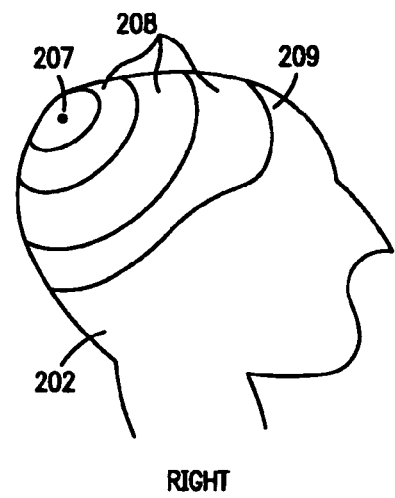

FIG. 2D illustrates an array of one circular disk-type electrode 207, a group of ring-type electrodes 208 concentrically arranged in irregular distances around the center circular disk-type electrode 207 and one irregular shaped ring-type electrode 209 on the mammalian head 202.

Figure 2E:
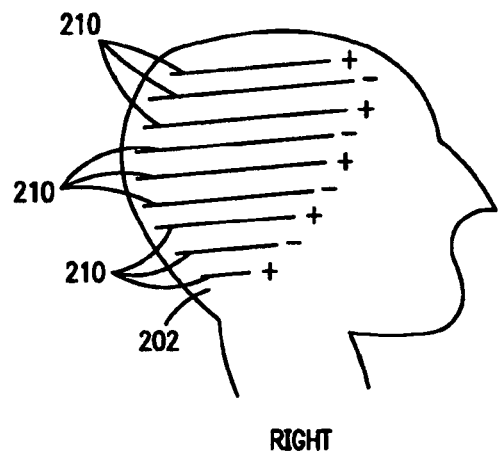

FIG. 2E illustrates a group of stripe-type electrodes 210 of different lengths, widths, and distances on one hemisphere of the mammalian head 202. In this particular embodiment of the present invention, the polarity, in any given moment of the stimulation, alternates between neighboring electrodes 210, indicated in the figure with the plus and minus polarity signs.

Figure 2F:
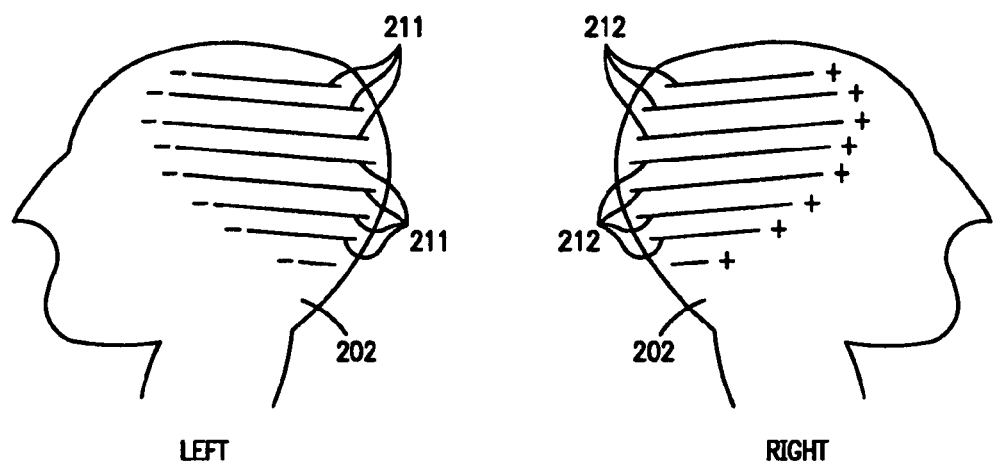

FIG. 2F illustrates two groups of stripe-type electrodes 211 and 212 of different lengths, width and distances on the mammalian head 202, one on the left hemisphere 211 and one on the right hemisphere 212. In this particular embodiment of the present invention, the polarity of the electrodes 211 of the left hemisphere are opposite to the polarity of the electrodes 212 of the right hemisphere, indicated in the figure with the plus and minus polarity signs.

Figure 2G:
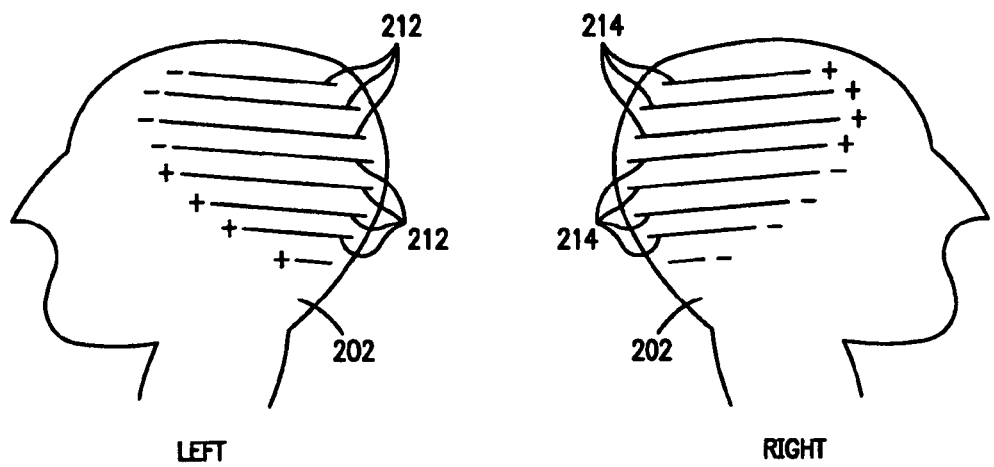

FIG. 2G illustrates two groups of regular or irregular shaped stripe-type electrodes 213 and 214 of different lengths, width and distances on the mammalian head 202, one on the left hemisphere 213 and one on the right hemisphere 214. In this particular embodiment of the present invention, the polarity of different subgroups of electrodes 213 and 214 varies at different times from the polarity of other subgroups, indicated in the figure with the plus and minus polarity signs. In this figure, two subgroups of electrodes comprise opposing polarities on each hemisphere at a particular moment. Alternatively, one or more subgroups could be neutral and not actively charged.

Figure 2H:
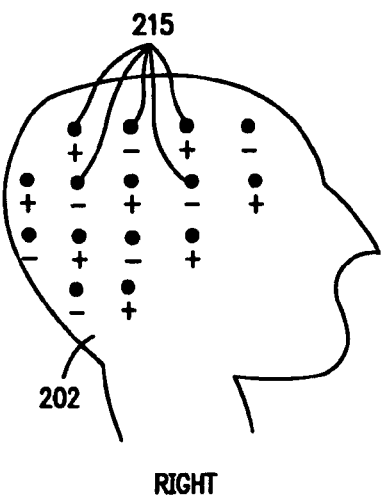

FIG. 2H illustrates a rectangular lattice of equally shaped disc-type electrodes 215 on the right hemisphere of the mammalian head 202. At a given moment, the polarity of the electrodes 215 alters such that each nearest neighbor electrode has opposing polarity, indicated in the figure with the plus and minus polarity signs.

Figure 2I:
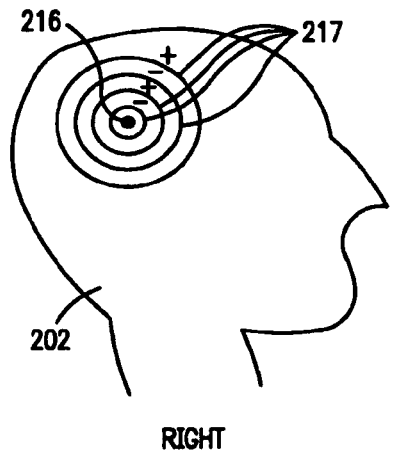

FIG. 2I illustrates a regular or irregular shaped disk-type electrode 216 surrounded by irregular shaped and unequally distanced ring type electrodes 217 on the right hemisphere of the mammalian head 202. At a given moment, the polarity the electrodes 216 and 217 alters such that each nearest neighbor electrode has opposing polarity, indicated in the figure with the plus and minus polarity signs. In the electrode system of FIG. 2D or FIG. 2I, the concentric ring structure of shown electrodes can be used as Laplace electrodes for sensing or detecting signals by building differences between different rings and/or the center electrode.

Figure 2J:
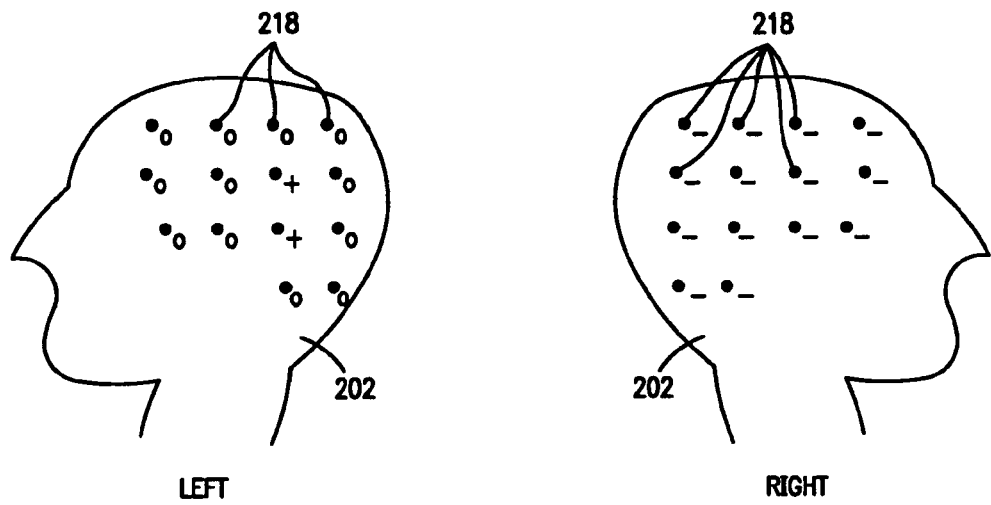

FIG. 2J illustrates two rectangular lattice groups of similar shaped disc-type electrodes 218, one group of the right hemisphere and one group on the left hemisphere of the mammalian head 202. In this embodiment of the present invention, at a given moment, the polarity of all of the electrodes 218 on the right hemisphere is negatively charged, while some electrodes 218 on the left hemisphere are positively charged and others on the left hemisphere are left neutral, as indicated in the figure with polarity signs pluses, minuses and zeros.

Figures 2K, 2L:
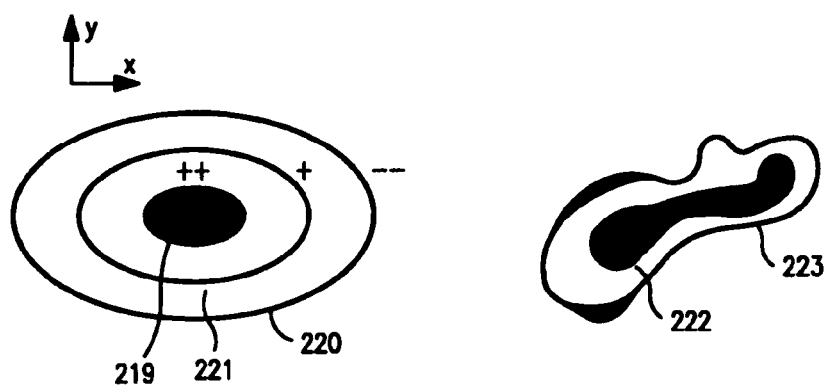

FIG. 2K illustrates an elliptical tripolar ring electrode or tripolar Laplace electrode. Heads of humans are irregular but in general spherically shaped. When the tripolar Laplace electrode is positioned on a spot of the head that is more curved in x- than in y direction, the elliptical shape of the electrode will compensate for this anisotropic deviation of the spherical head geometry. In this figure, center disc electrode 219 is, at a given moment, positively charged and outer disc electrode 220 is negatively charged. The middle disc electrode 221 is charged slightly positive.

FIG. 2L illustrates an irregular shaped targeted electrode. The shape as shown may result from the medical need to stimulate a certain irregular shaped area that may be an irregular shaped epileptic focus of the brain. Any type of regular or irregular shape may be utilized here. In the embodiment illustrated, the targeted electrode comprises an irregular shaped center disc electrode 222 and an irregular shaped ring electrode 223, the shape of which differs from the shape of the center electrode 222. In one embodiment of the present invention, an irregular shaped targeted electrode comprises more than two rings.

If an array of a large number of single disc electrodes is positioned around the 5 patient's head, any number of electrodes can be phased to operate together. In one embodiment of the present invention, those electrodes of the large electrode array are phased to yield a large Laplace electrode.

If the electrical contact between the rings of the Laplace electrodes to the tissue is not sufficient, the rings wilt break up in segments, and some segments will have contact while others will not; thus the ring electrodes may not function as Laplace but rather function as multi bipolar electrodes.

Concentric Ring/Laplace Electrodes

Laplace electrodes or concentric ring electrodes consist of a central disc and one or more concentric rings. Applying a voltage between the central disc and the ring or rings results in current flow between the disc and rings. The current distribution is dependent on the electrical properties of tissue and bone structure under the rings and on how the disc and rings are excited. For the purposes of this discussion, we will assume the model that homogeneous conductivities in the different layers of tissue is adequate, and focus primarily on single ring electrodes. There are two main differences between the Laplace electrodes or concentric ring electrodes and the conventional disc electrodes, as characterized by the current distribution within the head.

First, due to the ring electrode's cylindrical symmetry, the electric field and current density will also have cylindrical symmetry, assuming the medium is homogeneous. This cylindrical symmetry forces the current directly under the center of the ring to be perpendicular to the electrode. This is in contrast to a pair of disc electrodes, where the current at the midpoint between the electrodes is parallel to the electrodes. The different electric field orientations imply that the two types of electrodes will have different physiological effects when used for brain stimulation.

Second, the difference is due to the distributed nature of the ring electrode. In general, for a given excitation, the current density at the ring electrode will be smaller than the current density at the central disc electrode. Overall, for the Laplace electrodes or concentric ring electrodes, the current density is highest along its central axis for all depths, which provides an improved ability to localize stimulation. In contrast, for disc electrodes, the current density at both discs is the same and the position of maximum current density varies with depth.

Laplace electrodes or concentric ring electrodes are also useful for sensing electrical activity inside of the brain. Because the conductivity of the cerebral spinal fluid is high and the conductivity of the skull is low, these two layers form a low pass spatial frequency filter. Therefore, the resulting potential on the surface of the scalp due to cortical activity is blurred. It has been shown that applying a high spatial frequency filter, by calculating the surface Laplacian of the scalp potential, results in a signal that is very close to the cortical potential. Calculating the surface Laplacian from measurements of the surface potential at a grid of points is quite difficult, however, and it requires careful interpolation between the measurement electrodes. Laplace electrodes are configured to directly measure the surface Laplacian, and with the proper electronics, provide a higher fidelity map of the surface Laplacian.

The connection between the Laplace electrodes or concentric ring electrodes use for sensing and their use as stimulating electrodes can be made through the well known Lead Field Theory which states that the sensitivity of an electrode to a dipole source of current is proportional to the current density generated by the electrode when it is reciprocally energized. In other words, in order to calculate the voltage at an electrode due to a dipole current source, one can calculate the current distribution generated by driving a unit of current through the electrode and then take the inner product between the dipole current source and the current distribution. Specifically, $$V_{LE} = \int \frac{1}{\sigma} J_{LE} \cdot J^i dV$$

Where $V_{LE}$ is the measured voltage difference across the electrode, $J_{LE}$ is the current density distribution when the electrode is driven with IA of current, $J_i$ is the volume dipole source density, and $\sigma$ is the conductivity of the tissue. Because the Laplace electrodes or concentric ring electrodes are sensitive to the cortical potential directly underneath the electrode and insensitive to the cortical potential away from the electrode, we can infer that stimulation through these electrodes, $J_{LE}$, will be similarly localized.

The intuitive description of the performance of the Laplace electrodes or concentric ring electrodes and the prediction of Lead Field Theory are supported by numerical calculations of the current density in a layer cylindrical model of the head. Shown in FIG. 3A are the results for a concentric ring or Laplace electrode having a 2 mm diameter center disc and a 2 cm (centimeter) diameter, with a 1 mm (millimeter) wide ring, typically used for sensing that is not optimized for stimulation.

This model illustrates a number of features characteristic of the concentric ring or Laplace electrodes. First, as indicated above, the maximum current density in the brain occurs along the central axis of the electrode, and the current flow under the center electrode is in the vertical direction (see FIG. 3Ab). The effect of the high conductivity scalp and low conductivity skull, causing the majority of the current to be shunted by the scalp is illustrated by the three orders of magnitude drop in current density from the scalp surface to the surface of the brain (see FIG. 3Ac). The maximum current density that can be tolerated at the scalp will determine the maximum current density achievable at the brain surface. The maximum current density at the scalp occurs at the edges of the electrodes (see FIG. 3Ad) and is considerably higher than the surface current density at the center of the electrode.

Figure 3A:
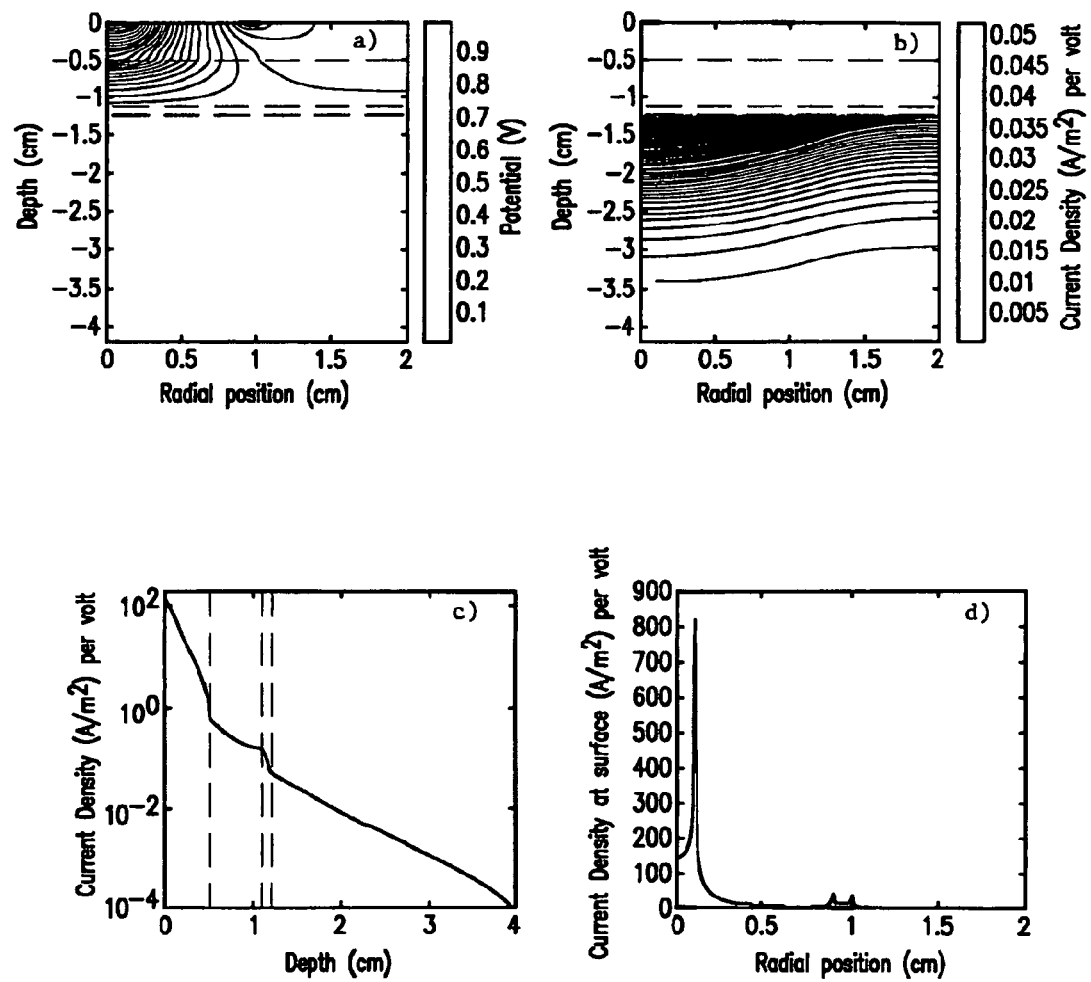
FIG. 3A illustrates the results of a numerical simulation of the electric field for an electrode with 2 mm central disc, 2 cm diameter, and 1 mm wide ring typical of a Laplace electrode for recording. Potential of central disc is 1V and of 20 the ring 0V. a) Contours of constant potential, b) contours of constant current density, arrows indicate direction of flow, c) current density along central axis, d) current density at the surface of the scalp.

The dashed lines in FIG. 3A represent the boundaries between the scalp, skull, cerebral spinal fluid, and the brain. Electrical conductivities and dimensions are presented in Table I, herein. Calculations were performed using a finite difference approximation to the continuity equation.

For stimulation, the electrode geometry should be optimized to deliver the maximum possible current to the surface of the brain and to minimize the current density at the scalp. The specific thresholds for current density required to stimulate neurons and also for burn generation in the scalp are not well known.

For deep brain stimulation, electric fields between 133V/m (Volt per meter) and 5 1.33 kV/m (kilo volts per meter) will produce transmembrane potentials between 1 mV (millivolts) and 1V in the range for stimulation, which for our model, correspond to current densities of 30 $A/m_2$ (amperes per square meter) and 300 $A/m_2$. For transcranial direct current stimulation, calculated current densities of only 0.1 $A/m_2$ were found to be in the range required to affect neural activity. In measurements of current density induced by transcranial magnetic stimulation, maximum values of 0.12 $A/m_2$ were recorded for 7% (percent) of the maximum stimulator output. In another numerical study, the current densities for electroconvulsive therapy and transcranial magnetic stimulation were calculated to be 234 $A/m_2$ and 322 $A/m_2$, respectively. Finally, for inducing motor evoked potentials, current densities between 2.5 $A/m_2$ and 6 $A/m_2$ were required. The range of current densities spans three orders of magnitude. For the purposes of discussion, a target current density of 10 $A/m_2$ is selected.

The generation of skin burns due to electrical stimulation is also not well understood. A variety of mechanisms are thought to be important, including electrolysis and oxygen/hydrogen gas bubble generation, pH changes in the tissue, and thermal damage. In all cases, the current density is a factor because electrochemical activity and power dissipation are proportional to the current density. The details of the damage process, however, are sensitive to the type of stimulation and stimulation parameters, such as monophasic (net current delivered) or biphasic (zero net current) stimulation, total charge delivered, pulsed stimulation parameters, and duration of the stimulation. Steady current densities less than 5 $A/m_2$ are considered safe, and for radiofrequency leakage currents, current densities less than 1000 $A/m_2$ for 10 seconds are required to prevent lesions. For the purposes of discussion, a maximum skin surface current density of 300 $A/m_2$ is selected. The optimization goal is therefore to achieve a ratio of brain current density to maximum current density of at least 0.03.

Figure 3B:
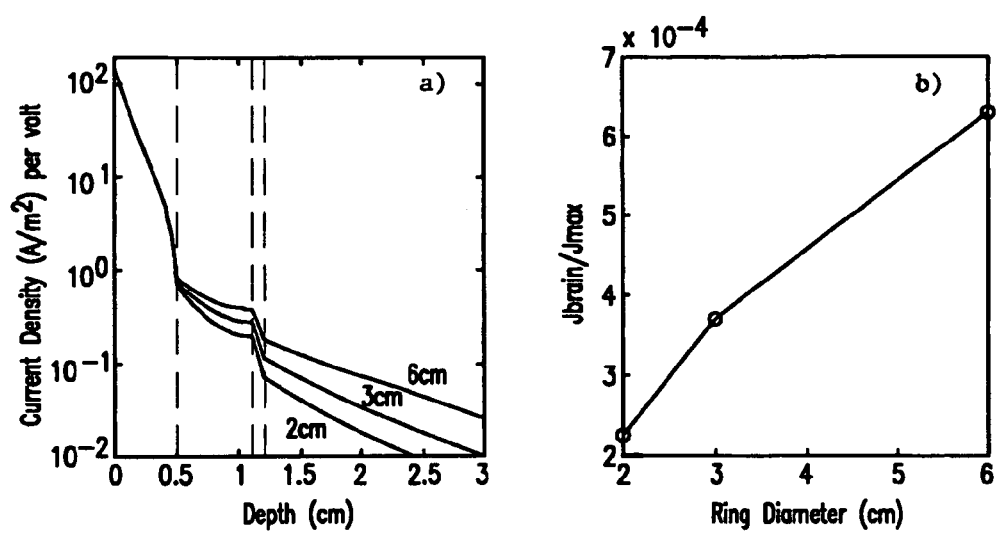
FIG. 3B illustrates the results of a numerical simulation of the electric field for an electrode having 2 cm, 3 cm, and 6 cm ring diameters. Central disc is 2 25 mm in diameter and rings are 1 mm wide. a). Current density along central axis. (dashed lines demarcate the scalp, skull, CSF, and brain), b) ratio of current density at the brain surface to the maximum current density at the edges of the electrode.

The depth of penetration is expected to increase with increasing ring diameter because for larger rings current paths that cross the skull and into the brain become more competitive with current paths through the scalp. Potential distributions and current densities were calculated for electrodes having 2 mm diameter discs and with rings having 2 cm, 3 cm, and 6 cm diameters and 1 mm width. The results for the potentials and current distribution are qualitatively the same as in FIG. 3A. Shown in FIG. 3B are the current densities at the electrode axis for three different diameter rings, along with the ratio of the current density at the brain to the maximum current density. The ratio improves with larger ring diameter, however, even for the 6 cm diameter ring it is only 0.0006, almost 50 times smaller than desired.

Figure 3C:
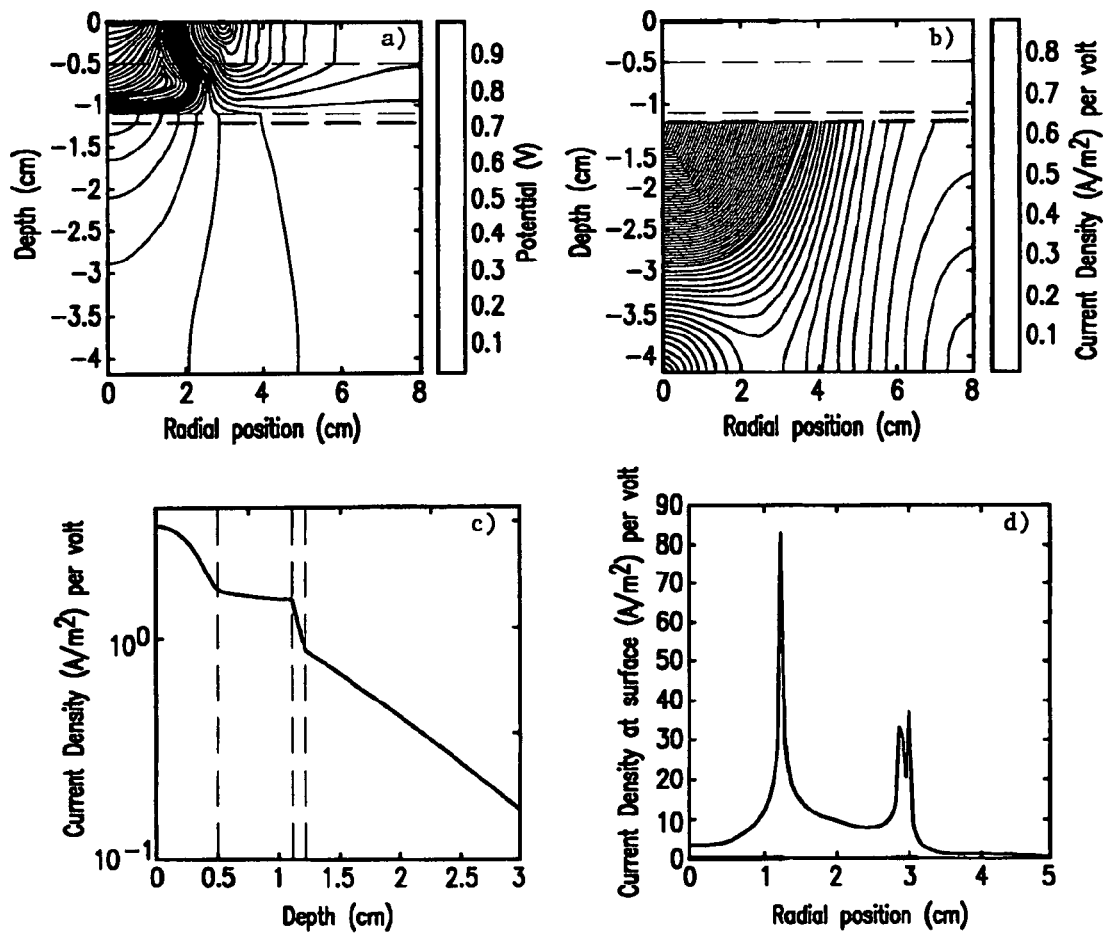
FIG. 3C illustrates the results of a numerical simulation of the electric field for an electrode having a 2.5 cm central disc with a 6 cm diameter, and a 1 mm 30 wide ring. Potential of the central disc is 1V and of the ring is 0V. a) Contours of constant potential, b) contours of constant current density, arrows indicate direction of flow, c) current density along central axis, d) current density at the surface of the scalp.

Further improvements in the penetration depth of the current can be achieved by increasing the disc diameter. The reasoning behind this is that the curvature in the potential or lateral spread of the current starts from the edges of the electrode and moves inward with depth. A larger disc electrode will be able to maintain a flat potential profile in the center with downward projecting current to a greater depth. In the limit of an infinitely large electrode, all of the current would be downward projecting. FIG. 3C shows the potential profiles and current distribution along with the central axis and surface current densities for a 2.5 cm diameter disc, with a 6 cm diameter ring having a 1 mm width.

Qualitative and quantitative differences can be observed between configurations illustrated in FIG. 3C and FIG. 3A. First, the squareness of the potential profile projects through the skull, and the current density at the surface is 12.4 times higher than for the case shown in FIG. 3A. When comparing electrodes with the same 6 cm diameter ring, the 2.5 cm disc electrode has a 4.8 times higher current density at the brain surface than the 0.2 mm diameter disc. The reduced current spreading near the central axis is also indicated by the small drop in current density across the skull, indicating that near the center most of the current is projected downward. Conversely, the high conductivity cerebral spinal fluid encourages current spreading and causes a sharp drop in current density that penetrates into the brain.

Figure 3D:
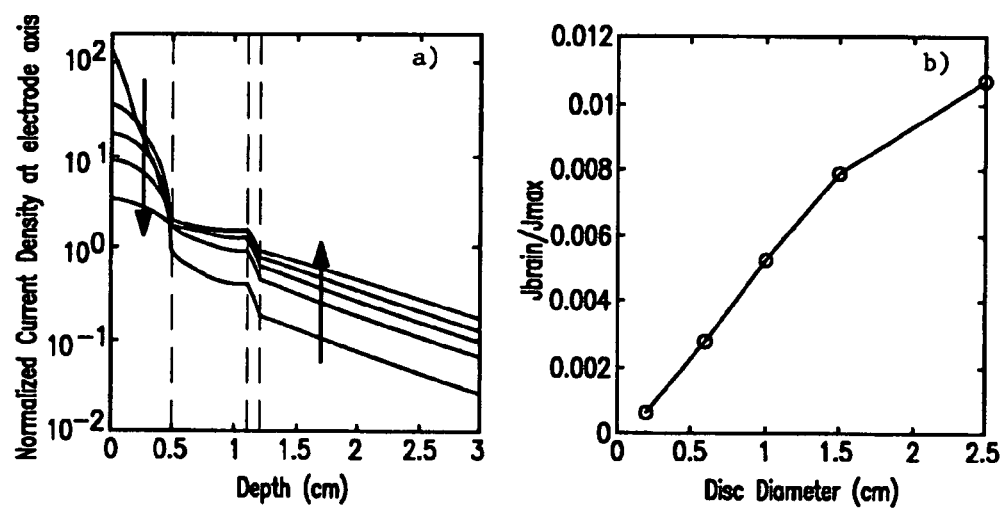
FIG. 3D illustrates the results of a numerical simulation of the electric field for an electrode having 0.2 cm, 0.6 cm, 1 cm, 1.5 cm, and 2.5 cm diameter discs 5 with a 6 cm diameter, and a 1 mm wide ring. a) Current density along central axis. (dashed lines demarcate the scalp, skull, CSF, and brain) Arrows indicate direction of increasing disc diameter, b) ratio of current density at the brain surface to the maximum current density at the edges of the electrode.

FIG. 3D shows the current density along the central axis and the ratio of the current density at the brain surface to the maximum current density at the scalp. The arrows indicate increasing disc diameter from 0.2 mm, 0.6 mm, 1 cm, 1.5 cm, and 2.5 cm. Increasing disc diameter also reduces the maximum current density at the surface because the larger perimeter allows for more gradual current spreading at the surface. The best case configuration with a 2.5 cm diameter disc, with a 6 cm diameter ring having a 1 mm width ring has a central axis brain current density to maximum surface current density ratio of 0.011, which is only 2.8 times smaller than our target of 0.03.

From FIG. 3C, the limiting factor in the brain surface to scalp surface current density ratio is the high current density at the edge of the electrode. This is primarily due to the sharp transition in the potential radially from the edge of the electrode. A possible solution is to attempt to gradually generate a smoother transition in the potential, perhaps by engineering the electrode-skin interface impedance, as has been explored for cardiac defibrillator electrodes.

Figure 3E:
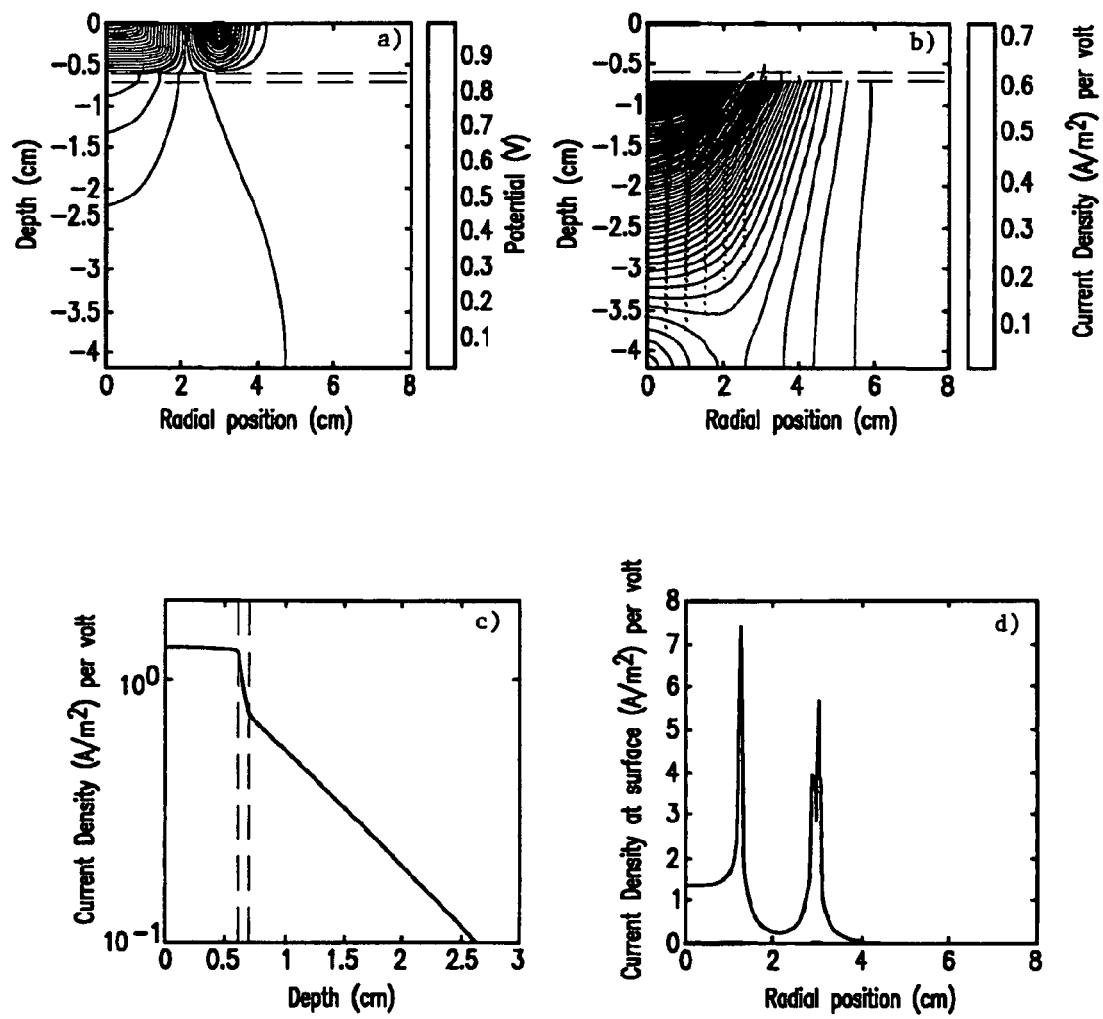
FIG. 3E illustrates the results of a numerical simulation of the electric 10 field for an electrode with 2.5 cm central disc and 6 cm diameter, 1 mm wide ring. Potential of central disc is 1V and of the ring is 0V. a) Contours of constant potential, b) contours of constant current density, arrows indicate direction of flow c) current density along central axis, d) current density at the surface of the skull.

Another alternative to achieving a high current density in the brain is to avoid shunting by the scalp via implanting electrodes directly on the skull. Such an approach would require addressing long-term electrode maintenance problems and increased invasiveness, but with the benefits of more efficient current delivery to the brain. FIG. 3E shows the potential and current distributions along with the central axis current density and surface current density for a 2.5 cm diameter disc having a 6 cm diameter, and 1 mm wide ring in direct contact with the skull, and with the entire region above the electrode completely insulated from the surrounding scalp (no current flow in scalp). In this case, the ratio of the brain surface current density and the maximum current density on the skull is 0.1, much larger than the cases where the electrodes are on the scalp. Although this parameter is not as relevant as we are not so concerned with burning of the skull, it does indicate that a much higher percentage of the total current is delivered to the brain.

In this case, the largest source of current loss is shunting by the cerebral spinal fluid (CSF) layer. However, the current density at the brain surface is not very sensitive to the thickness of the CSF layer, decreasing from 0.73 A/m$_2$ for a 1 mm thick CSF to 0.58 A/m$_2$ for a 1.5 mm thick CSF, and 0.51 A/m$_2$ for a 2 mm thick CSF. These numerical results confirm the general properties of the concentric ring or Laplace electrodes insofar as the lateral localization of the current density stimulation and the perpendicular orientation of the current in the stimulation zone. Preliminary optimization of the electrodes for stimulation points to the use of a large disc electrode with a single concentric ring. Improved performance with respect to the surface current density can potentially be obtained by engineering the electrode-skin interface such that the excitation potential gradually decays towards the edges of the electrode. Table I summarizes the characteristics of the numerically simulated electrodes.

These results are primarily of qualitative value and provide a useful guide for further optimization of the concentric ring or Laplace electrodes for stimulation. Quantitative errors between the model and an actual human head limit the confidence in the numerical results. In addition, the electrode-skin interface was not modeled, resulting in relatively low electrode impedances. Inclusion of this phenomenon and adding the capability to model a radially varying electrode-skin interface will lead to better optimized electrodes for stimulation. In addition, higher resolution sampling of the electrodes using a structured mesh, especially near their edges where the current density is maximal, would be beneficial in order to improve the accuracy of the results. Preliminary efforts at optimization of the concentric ring or Laplace electrodes for stimulation resulted in a 48 times improvement in the brain current density to surface current density ratio, and 12 times reduction in voltage required to produce 10 A/m$_2$ of current density at the surface of the brain. Current densities to stimulate the brain span a range typically from about 0.1 A/m$_2$ to about 300 A/m$_2$, but can also go up to 1300 A/m$_2$.

Electrode Control Electronics

Control of the treatment can involve one or more of the following; A) performing the algorithm for sensing and calculating the impedance of all combinations of electrode poles and electrode pairs, B) configuration and connection of electrodes for the sensing of electrical activity, C) 2- or 3-dimensional modeling of the sensed activity to identify and detect the location to be targeted, D) computation of the most favorable electrode activation to treat the targeted area, E) configuration and connection of electrodes to deliver optimal treatment, F) delivery of energy to electrodes in the amount and for the duration calculated in step D, and G) a summary of the data detected, the software's logic steps, and the current waveforms delivered to the patient is generated and stored.

Determining impedances from pole to pole or from electrode to electrode can be a simple measure of DC current for a given DC voltage, or it can be a complex AC impedance analysis. The data is used in calculating the necessary voltage to achieve a therapeutic level of current in the targeted tissue. It can also be used as a measure of the quality of the elec-

TABLE I

CHARACTERISTICS OF SIMULATED ELECTRODES

| Parameter | Unit | Scalp, small disc, varying ring diameter | | | | Scalp, increasing diameter disc | | | Skull electrode |
|---|---|---|---|---|---|---|---|---|---|
| Disc diameter | cm | 0.2 | 0.2 | 0.2 | 0.6 | 1 | 1.5 | 2.5 | 2.5 |
| Ring diameter | cm | 2 | 3 | 6 | 6 | 6 | 6 | 6 | 6 |
| Ring width | cm | 0.1 | 0.1 | 0.1 | 0.1 | 0.1 | 0.1 | 0.1 | 0.1 |
| $J_{brain}/J_{surface}$ | ×10$^{-4}$ | 2.2 | 3.7 | 6.3 | 28 | 52 | 79 | 107 | 988 |
| % current delivered to Brain | | 0.6 | 2 | 10 | 10.6 | 11.1 | 11.2 | 11 | 51.4 |
| % current shunted by Scalp | | 96.7 | 93.1 | 80.2 | 79.3 | 78.7 | 78.6 | 79.3 | 0 |
| % current shunted by skull | | 1.9 | 2.9 | 3.1 | 3.1 | 3.1 | 3.1 | 3 | 12.6 |
| % current shunted by CSF | | 0.7 | 2 | 6.7 | 6.9 | 7.1 | 7.1 | 6.7 | 36 |
| Electrode impedance | Ω | 858 | 891 | 939 | 414 | 287 | 210 | 133 | 965 |
| Voltage for 10 A/m$^2$ at brain | V | 140 | 88 | 55 | 23 | 16 | 13 | 11 | 14 |
| Surface Current density at threshold | 10$^4$ A/m$^2$ | 4.5 | 2.7 | 1.6 | 0.36 | 0.19 | 0.12 | 0.09 | 0.01 |
| Power dissipation at threshold voltage | W | 24.2 | 9.1 | 3.3 | 1.2 | 0.9 | 0.8 | 0.94 | 0.2 | trodes' electrical contact to the skin/scalp and to alert the clinician to the existence of a poor connection between the electrode and the patient.

The electrodes are electronically switched to circuits designed to monitor biological electrical activity in the brain. In this circuit, the electrodes act as antennae with poles either on the same electrode or between pairs of electrodes. The resulting waveforms can be used to determine the amplitude, shape and frequency of the electrical activity in the various portions of the brain.

If the position of each electrode is known, the data can be processed to yield a 3-dimensional map of brain electrical activity. Using this map, the appropriate electrodes can be energized and the areas of the brain to be treated can be limited to only those areas in which abnormal electrical activity is present.

The electrical activity can be compared to a data base of known electrical anomalies associated with the condition to be treated. The treatment can then be optimized for the type of abnormal activity being exhibited. Using the impedance data from step A, the position data from step C and the results of the comparison above, the treatment voltage waveform applied to the electrodes or electrode pairs can be customized to deliver current in the targeted area that has an amplitude, wave form and frequency, known to have the highest likelihood of success for the type of disorder detected. If the electrical activity is not recognizable by the software algorithm or if a specific treatment area is not distinguishable, then the device can offer the clinician the option of administering a default, general treatment to more than one area and possibly a series of treatments to all areas.

The appropriate electrodes can then be electronically switched into the treatment delivery circuit and connected to one or more programmable power supplies.

The optimized voltage waveform calculated in step D can then be applied to the appropriate electrodes. Before application of voltage to the electrodes, a summary of the results of step A through step E can be displayed and the clinician can be offered the option of continuing or discontinuing the treatment.

All pertinent data and information gathered and generated during steps A through F can be stored electronically and/or printed out for the patient's records and for improving the treatment algorithm. With an appropriate rating scheme for patient outcomes, the software and its associated databases may be improved using standard software evolutionary techniques.

Targeting Electrodes

On the basis of the well known reciprocity theorem of electric fields, which states that the radiation and receiving patterns of an antenna are identical, WO/2006/044793 teaches that ideal concentric ring electrodes can be used to sense and stimulate targeting brain areas with targeting electrodes consisting of a central disc and one or more concentric rings.

However, in addition, targeting electrodes being described herein can also be regular or irregular shaped ring or concentric electrodes, or symmetrical or unsymmetrical shaped ring or concentric ring electrodes. Further, the targeting electrodes as described here are adjusted to the seizure focus of the particular patient. In one embodiment, dynamic adjustment is provided for electrodes of any type, by a switching system, to adapt dynamically to moving foci.

In one example, as described hereinbelow, a ring structure of the targeting electrodes can be constructed by electrically connecting a number of discrete electrodes in an array together. Application of voltage between the central disc and the ring or rings results in current flow between the disc and rings. The current distribution is dependent on the electrical properties of tissue and bone structure under the rings and on how the disc and rings are excited. For the purposes of this discussion, we will assume that: a) the concentric ring targeting electrode discussed here is an ideal concentric ring electrode, and b) the model that homogeneous conductivities in the different layers of tissue is adequate, and focus primarily on single ring electrodes. Because the human head is irregularly shaped in 3-dimensions the idea of an ideal flat concentric ring is therefore just a model for the ease of the discussion. In a similar way as described for concentric ring electrodes, the model described herein can be applied to a targeting electrode constructed from an array of discrete discs, or electrodes of virtually any construction, as outlined hereinbelow.

There are two main differences between targeting or concentric ring electrodes and the conventional disc electrodes, as characterized by the current distribution within the head. First, due to the ring electrode's cylindrical symmetry, the electric field and current density will also have cylindrical symmetry, assuming the medium is homogeneous. This cylindrical symmetry forces the current directly under the center of the ring to be perpendicular to the electrode. This is in contrast to a pair of disc electrodes, where the current at the midpoint between the electrodes is parallel to the electrodes. The different electric field orientations imply that the two types of electrodes will have different physiological effects when used for brain stimulation.

Second, the difference is due to the distributed nature of the ring electrode. In general, for a given excitation, the current density at the ring electrode will be smaller than the current density at the central disc electrode. Overall, for the concentric ring electrodes, the current density is highest along its central axis for all depths, which provides an improved ability to localize stimulation. In contrast, for disc electrodes, the current density at both discs is the same and the position of maximum current density varies with depth.

Concentric ring electrodes are also useful for sensing electrical activity inside of the brain. Because the conductivity of the cerebral spinal fluid is high and the conductivity of the skull is low, these two layers form a low pass spatial frequency filter. Therefore, the resulting potential on the surface of the scalp due to cortical activity is blurred. It has been shown that applying a high spatial frequency filter, by calculating the surface Laplacian of the scalp potential, results in a signal that is very close to the cortical potential. Calculating the surface Laplacian from measurements of the surface potential at a grid of points is quite difficult, however, and it requires careful interpolation between the measurement electrodes. Laplace electrodes are configured to directly measure the surface Laplacian, and with the proper electronics, provide a higher fidelity map of the surface Laplacian.

The connection between the concentric ring electrodes use for sensing and their use as stimulating electrodes can be made through the well known Lead Field Theory which states that the sensitivity of an electrode to a dipole source of current is proportional to the current density generated by the electrode when it is reciprocally energized. In other words, in order to calculate the voltage at an electrode due to a dipole current source, one can calculate the current distribution generated by driving a unit of current through the electrode and then take the inner product between the dipole current source and the current distribution. Specifically, $$V_{LE} = \int \frac{1}{\sigma} J_{LE} \cdot J^i dV$$

Where $V_{LE}$ is the measured voltage difference across the electrode, $J_{LE}$ is the current density distribution when the electrode is driven with 1 A of current, $J^i$ is the volume dipole source density, and $\sigma$ is the conductivity of the tissue. Because concentric ring electrodes are sensitive to the cortical potential directly underneath the electrode and insensitive to the cortical potential away from the electrode, we can infer that stimulation through these electrodes, $J_{LE}$, will be similarly localized.

The intuitive description of the performance of the Laplace electrodes or concentric ring electrodes and the prediction of Lead Field Theory are supported by numerical calculations of the current density in a layer cylindrical model of the head.

Figure 9:
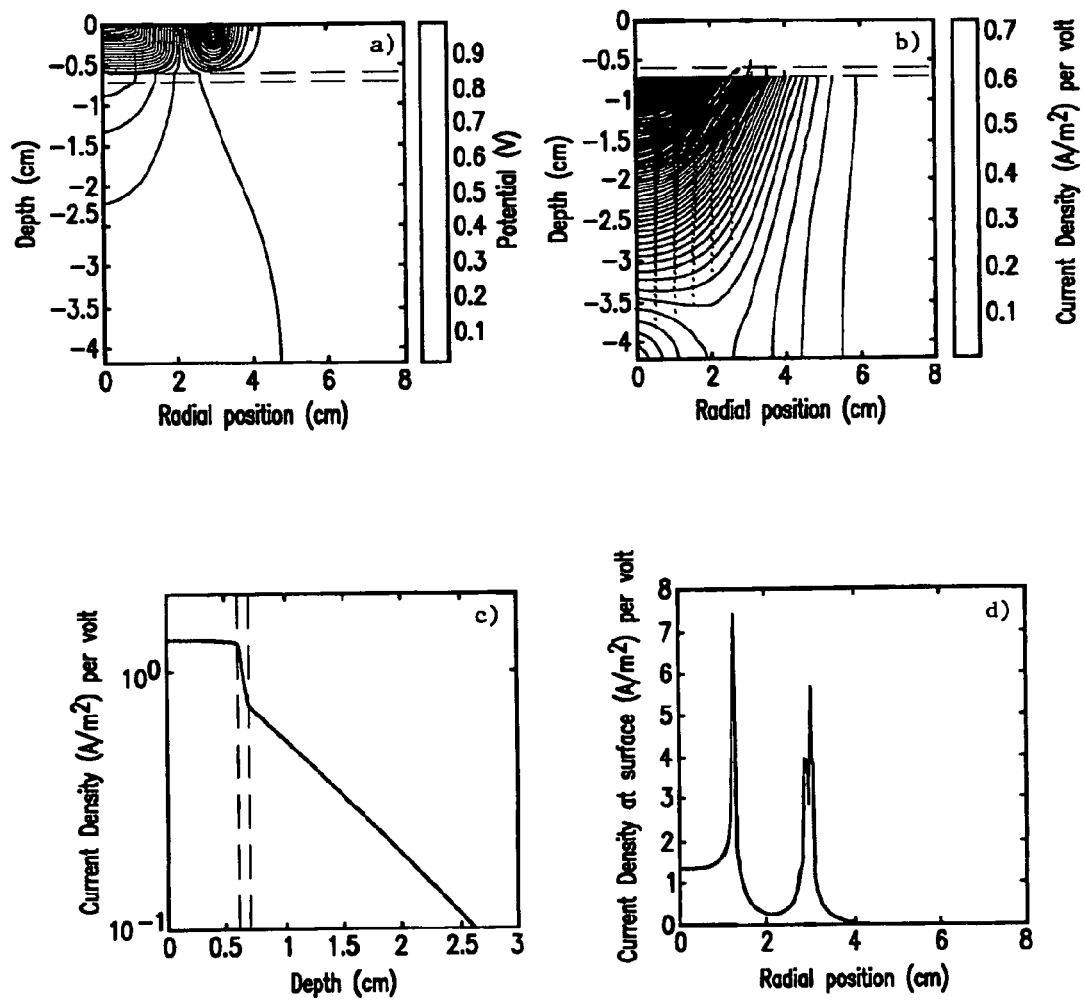
FIG. 9 illustrates the results of a numerical simulation of the electric field for an electrode having a 2.5 cm central disc and 6 cm diameter, 1 mm wide ring. Potential of central disc is 1 V and of the ring is 0 V. Graphs a)-d) show the following: a) contours of constant potential, b) contours of constant current density, arrows indicate direction of flow, c) current density along central axis, and d) current density at the surface of the skull.

FIG. 9 shows the potential and current distributions along with the central axis current density and surface current density for a 2.5 cm diameter disc having a 6 cm outer diameter, and 1 mm wide ring in direct contact with the skull, and with the entire region above the electrode completely insulated from the surrounding scalp (no current flow in scalp).

In this case, the largest source of current loss is shunting by the cerebral spinal fluid (CSF) layer. However, the current density at the brain surface is not very sensitive to the thickness of the CSF layer, decreasing from 0.73 A/m$^2$ for a 1 mm thick CSF to 0.58 A/m$^2$ for a 1.5 mm thick CSF, and 0.51 A/m$^2$ for a 2 mm thick CSF.

The dashed lines in FIG. 9 represent the boundaries between the skull, cerebral spinal fluid, and the brain. Electrical conductivities and dimensions are presented in Table II. Calculations were performed using a finite difference approximation to the continuity equation.

TABLE II

HEAD MODEL PARAMETERS

| Tissue | Conductivity (S/m) | Thickness (cm) |
|---|---|---|
| Skull | 0.014 | 0.6 |
| Cerebral Spinal Fluid | 1.792 | 0.1 |
| Brain | 0.224 | 3.0 |

This model illustrates a number of features characteristic of the concentric ring electrodes. First, as indicated above, the maximum current density in the brain occurs along the central axis of the electrode, and the current flow under the center electrode is in the vertical direction.

For stimulation, the electrode geometry should be optimized to deliver the maximum possible current to the surface of the brain and to minimize the current density at the scalp. A switching system is disclosed in an example of an efficient operating system capable of dynamic optimization. The specific thresholds for current density required to stimulate neurons and also for burn generation in the scalp are not well known.

For deep brain stimulation, electric fields between 133 V/m (Volt per meter) and 1.33 kV/m (kilo volts per meter) will produce transmembrane potentials between 1 mV (milli volts) and 1 V in the range for stimulation, which for our model, correspond to current densities of 30 A/m$^2$ (amperes per square meter) and 300 A/m$^2$. For transcranial direct current stimulation, calculated current densities of only 0.1 A/m$^2$ were found to be in the range required to affect neural activity. In measurements of current density induced by transcranial magnetic stimulation, maximum values of 0.12 A/m$^2$ were recorded for 7% (percent) of the maximum stimulator output. In another numerical study, the current densities for electroconvulsive therapy and transcranial magnetic stimulation were calculated to be 234 A/m$^2$ and 322 A/m$^2$, respectively. Finally, for inducing motor evoked potentials, current densities between 2.5 A/m$^2$ and 6 A/m$^2$ were required. The range of current densities spans three orders of magnitude. For the purposes of discussion, a target current density of 10 A/m$^2$ is selected.

The generation of skin burns due to electrical stimulation is also not well understood. A variety of mechanisms are thought to be important, including electrolysis and oxygen/hydrogen gas bubble generation, pH changes in the tissue, and thermal damage. In all cases, the current density is a factor because electrochemical activity and power dissipation are proportional to the current density. The details of the damage process, however, are sensitive to the type of stimulation and stimulation parameters, such as monophasic (net current delivered) or biphasic (zero net current) stimulation, total charge delivered, pulsed stimulation parameters, and duration of the stimulation. Steady current densities less than 5 A/m$^2$ are considered safe, and for radiofrequency leakage currents, current densities less than 1000 A/m$^2$ for 10 seconds are required to prevent lesions. For the purposes of discussion, a maximum skin surface current density of 300 A/m$^2$ is selected.

The optimization goal is therefore to achieve a ratio of brain current density to maximum current density of at least 0.03.

The depth of penetration is expected to increase with increasing ring diameter because for larger rings current paths that cross the skull and into the brain become more competitive with current paths through the scalp. Potential distributions and current densities were calculated for electrodes having 2 mm diameter discs and with rings having 2 cm, 3 cm, and 6 cm diameters and 1 mm width.

Further improvements in the penetration depth of the current can be achieved by increasing the disc diameter. A larger disc electrode will be able to maintain a flat potential profile in the center with downward projecting current to a greater depth. In the limit of an infinitely large electrode, all of the current would be downward projecting.

When comparing electrodes with the same 6 cm diameter ring, the 2.5 cm disc electrode has a 4.8 times higher current density at the brain surface than the 0.2 mm diameter disc. The reduced current spreading near the central axis is also indicated by the small drop in current density across the skull, indicating that near the center most of the current is projected downward. Conversely, the high conductivity cerebral spinal fluid encourages current spreading and causes a sharp drop in current density that penetrates into the brain.

Another alternative to achieving a high current density in the brain is to avoid shunting by the scalp via implanting electrodes directly on the skull. Such an approach would require addressing long-term electrode maintenance problems and increased invasiveness, but with the benefits of more efficient current delivery to the brain.

These numerical results confirm the general properties of the concentric ring electrodes insofar as the lateral localization of the current density stimulation and the perpendicular orientation of the current in the stimulation zone. Preliminary optimization of the electrodes for stimulation points to the use of a large disc electrode with a single concentric ring.

Improved performance with respect to the surface current density can potentially be obtained by engineering the electrode-skin interface such that the excitation potential gradually decays towards the edges of the electrode. Table III summarizes the characteristics of the numerically simulated electrodes.

TABLE III

CHARACTERISTICS OF SIMULATED ELECTRODES

| Parameter | Unit | Skull electrode |
|---|---|---|
| Disc diameter | cm | 2.5 |
| Ring diameter | cm | 6 |
| Ring width | cm | 0.1 |
| $J_{brain}/J_{surface}$ | $\times 10^{-4}$ | 988 |
| % current delivered to Brain | | 51.4 |
| % current shunted by Scalp | | 0 |
| % current shunted by skull | | 12.6 |
| % current shunted by CSF | | 36 |
| Electrode impedance | ohms | 965 |
| Voltage for 10 A/m² at brain | V | 14 |
| Surface Current density at threshold | $10^4$ A/m² | 0.01 |
| Power dissipation at threshold voltage | W | 0.2 |

These results are primarily of qualitative value and provide a useful guide for further optimization of the concentric ring electrodes for stimulation. Quantitative errors between the model and an actual human head limit the confidence in the numerical results. Preliminary efforts at optimization of the concentric ring electrodes for stimulation resulted in a 48 times improvement in the brain current density to surface current density ratio, and 12 times reduction in voltage required to produce 10 A/m² of current density at the surface of the brain. Current densities to stimulate the brain span a range typically from about 0.1 A/m² to about 300 A/m², but can also go up to 1300 A/m². As will be seen stimulation can take many forms including continuous or discontinuous waves or wave patterns, pulse trains or very low frequency signals, or direct current. For example, cathodal DC stimulation can be employed as well as anodal DC stimulation. Thus, the present invention can be used for different clinical purposes. For example, cathodal direct current can be delivered to reduce seizure activity. or to treat hyperactivity or mania, while anodal direct current can be delivered to treat depression. In any event, cathodal or anodal direct current stimulation can be delivered constantly or recurrently in time intervals of constant or changing duration from subpericranial or subgaleal positioned electrodes, for example.

Targeting Disc-Array Electrodes

Figure 10A:
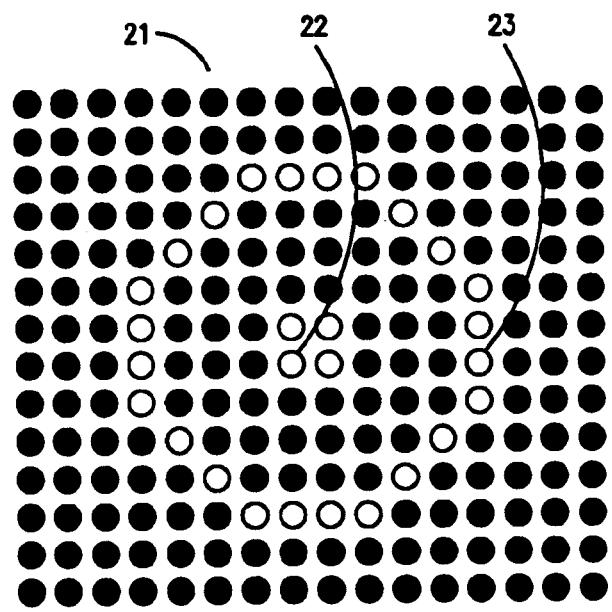
FIG. 10A illustrates a Targeting Disc-Array Electrode of 16×14 disc electrodes in which a concentric ring electrode is constructed by electrically connecting certain discs to yield a center and an outer pole, according to an embodiment of the present invention.

As disclosed in WO/2006/044793, a concentric ring electrode capable of delivering stimulation to a location in the brain is known. However, those concentric rings are fixed in shape and location. To overcome this disadvantage, one example of an epilepsy system of the present invention senses the EEG signal using an array of epicranial discrete electrodes, detects the presence and location of a seizure focus, and stimulates localized said focus by electrically connecting appropriate single discrete electrodes in said array to a targeting electrode. As an example, shown in FIG. 10A, is an array 11 of 16×14 equally spaced disc electrodes. Certainly when fixed onto (cutaneous) or under (subgaleal) the scalp, the shown flat two dimensional array, preferably flexible, will have a three-dimensional curvature. For the ease of discussion here, all n×m array electrodes will be assumed to be equally spaced and flat. However, arrays do not have to be rectangular or equally spaced. They can have any shape, including the shapes of quadrate, polygon, round or elliptical. Spaces between the discs can be equal over the entire array, equal only in certain directions within the array, or completely irregular, or any combination thereof. The discs can have any form, such as round, elliptic, quadrate, rectangular, polygon, irregular shaped, or any combination thereof. The discs within an array can all be shaped the same or differently. In one embodiment of the invention, one or more arrays can be used, of which some may be implanted subscalp and some cutaneous or some may be implanted intracranial.

With a switching network, any combination of electrodes in the n×m array can be connected together. As an example, shown in FIG. 10A, 4 disc electrodes 22 are connected and 12 electrodes 23 are connected. Together, the structure in the figure yields a concentric ring electrode in which the electrodes 22 build the inner disc pole and the electrodes 23 build the outer ring pole of a concentric ring electrode. The targeting benefits of a ring electrode are described in section 2 hereinabove. All other electrodes in the array are not used and left uncharged or neutral.

Figure 10B:
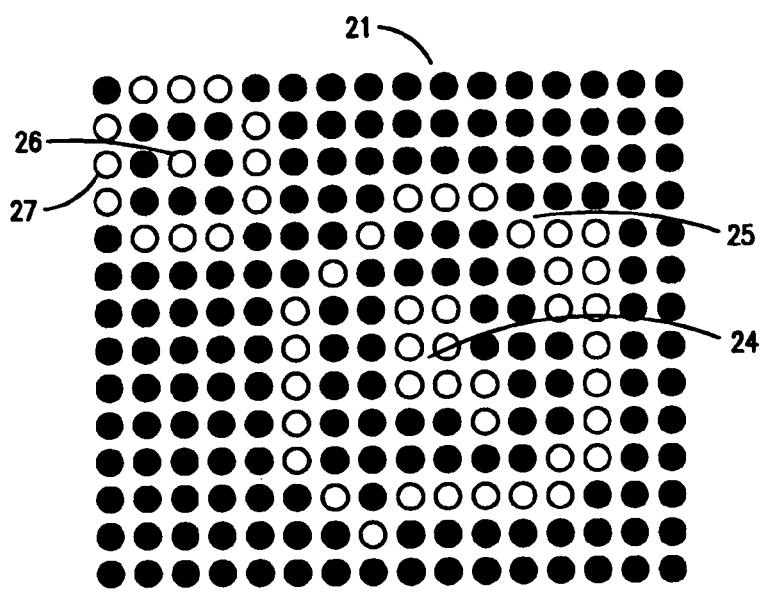
FIG. 10B illustrates a Targeting Disc-Array Electrode of 16×14 disc electrodes in which two irregular shaped ring electrode are constructed by electrically connecting individual disc electrodes, according to an embodiment of the present invention.

The array of disc electrodes can be used to build any type of targeting electrode or other transmissive structure. FIG. 10B shows another example in which disc electrodes 24 comprise the one pole and disc electrodes comprise the other pole of an irregular shaped ring electrode. Shown in the same array is a second ring electrode consisting of disc electrodes 26 as inner pole and electrodes 27 as outer pole. The reason for building two targeting electrodes may be that two seizure foci were detected and are found to be treatable by stimulation.

In one embodiment of the present invention, the targeting electrodes for sensing EEG signals or stimulating or both are located subpericranial or subgaleal. In one embodiment of the present invention, at least one reference electrode for sensing EEG signals or stimulating is located in a part of the body other than the subpericranial or subgaleal regions. In one preferred embodiment of the present invention, the reference electrode is the external surface of the container containing the power supply and/or current generator which is implanted in the body.

As a further example, in one embodiment of the present invention, a device for treating either epilepsy or depression consists of a single large subscalp electrode (or alternatively, an array of smaller electrodes of any type) applied to a specific region of the skull. A reference electrode a reference electrode is located in a convenient portion of the body, such as the subpectoral area. In the case of depression, the region is preferably pre-specified, and in the case of epilepsy, the region depends on the location of the seizure activity. In any event, the reference electrode preferably comprises the metal container containing the battery, and electronic circuitry of the type described herein. The container is preferably implanted in a convenient location of the body, such as the subpectoral region of the chest. If desired, the container can serve as the reference electrode. Such device could be employed to provide different effective therapies, such as a substrate modification mode delivering a pulse of DC or AC electrical current or other types of preventive signals considered herein, on a prescribed time basis, such as a chronic periodic basis.

Within an array of discrete electrodes, the Laplacian transformation that can be applied for EEG recordings, whereby one approximates the Laplacian of the electrical field at one location by using the measurements at neighboring disc electrodes. In theory, it is not really different from recording from a Laplacian electrode (the outer ring playing the same role as a set of discrete electrodes around a center electrode).

Dynamic Adaptation of Targeting Disc-Array Electrodes

By using the described disc-array electrodes with a switching network, any shape, form or type of targeting electrodes or other transmissive and/or sensing structure can virtually be constructed by simply digitally connecting any number of disc electrodes within the array of disc electrodes. This technique is especially useful in a dynamic environment, when the focus of a seizure dynamically changes its shape and/or position, and especially increases in size, e.g., when a partial seizure transforms into a generalized seizure or when the focus continues to move over time.

Figure 11:
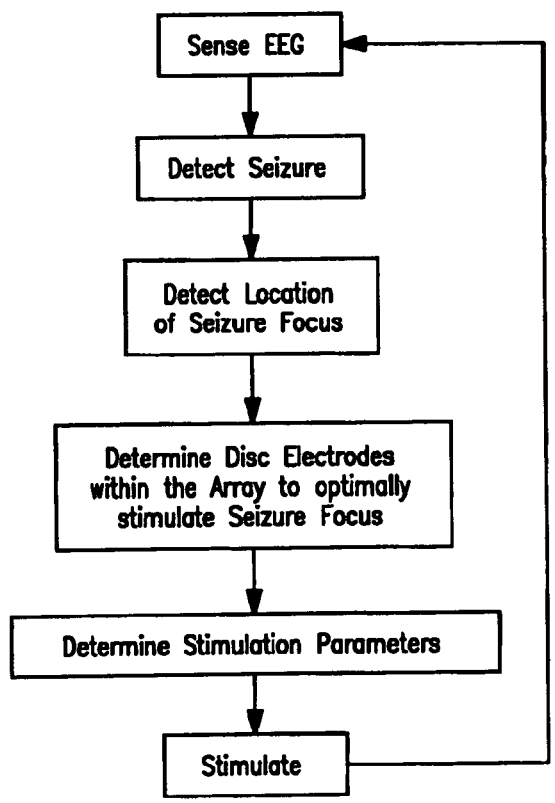
FIG. 11 shows a flow chart of an algorithm for the dynamic adaptation cycle of Targeting Disc-Array Electrodes, according to an embodiment of the present invention.

To dynamically adapt a Targeting Disc-Array Electrode to a moving or dynamically changing target, the form and location of the Targeting Disc-Array Electrode within the disc array is constantly adapted to optimally deliver the stimulation to the focus in sensing-stimulation cycles. In each cycle, as seen in FIG. 11, the disc electrodes of the array are used to sense the EEG signal distribution coming out of the brain. A seizure detection algorithm determines if a seizure exists and determines the location of the seizure focus. An optimization algorithm determines the exact discrete electrodes within the array and how they should be connected to form one or more targeting electrodes or other stimulating patters, to optimally stimulate the seizure focus. Further, the stimulation parameters of voltage, current amplitude, frequency, pulse rate, pulse duration, cycle duration and duty cycle, for example, are also determined. The stimulation is then carried out using the optimized disc electrode configuration and stimulation parameters; thereafter, a new cycle starts by sensing the EEG again. The shape, form or type of the Targeting Disc-Array Electrode and stimulation parameters an thus be constantly optimized from cycle to cycle and the entire system is capable of following and adapting to a moving focus or a dynamically changing focus (e.g. changes in shape, number of nodes, intensity distributions). Therefore, the Targeting Disc-Array Electrode will constantly adapt itself to the needs of the current treatment.

In one embodiment of the invention, the Targeting Disc-Array Electrode may be constructed to not only stimulate a seizure focus but also a margin around it.

Electrode Control Electronics

Control of the treatment can involve one or more of the following; A) performing the algorithm for sensing and calculating the impedance of all combinations of electrode poles and electrode pairs, B) configuration and connection of electrodes for the sensing of electrical activity, C) two- or three-dimensional modeling of the sensed activity to identify and detect the location to be targeting, D) computation of the most favorable electrode activation to treat the targeting area, E) configuration and connection of electrodes to deliver optimal treatment, F) delivery of energy to electrodes in the amount and for the duration calculated in step D, and G) a summary of the data detected, the software's logic steps, and the current waveforms delivered to the patient is generated and stored.

Determining impedances from pole to pole or from electrode to electrode can be a simple measure of DC current for a given DC voltage, or it can be a complex AC impedance analysis. The data is used in calculating the necessary voltage to achieve a therapeutic level of current in the targeted tissue. It can also be used as a measure of the quality of the electrodes' electrical contact to the skin/scalp and to alert the clinician to the existence of a poor connection between the electrode and the patient.

The electrodes are electronically switched to circuits designed to monitor biological electrical activity in the brain. In this circuit, the electrodes act as antennae with poles either on the same electrode or between pairs of electrodes. The resulting waveforms can be used to determine the amplitude, shape and frequency of the electrical activity in the various portions of the brain.

If the position of each electrode is known, the data can be processed to yield a 3-dimensional map of brain electrical activity. Using this map, the appropriate electrodes can be energized and the areas of the brain to be treated can be limited to only those areas in which abnormal electrical activity is present.

The electrical activity can be compared to a data base of known electrical anomalies associated with the condition to be treated. The treatment can then be optimized for the type of abnormal activity being exhibited. Using the impedance data from step A, the position data from step C and the results of the comparison above, the treatment voltage waveform applied to the electrodes or electrode pairs can be customized to deliver current in the targeted area that has an amplitude, wave form and frequency, known to have the highest likelihood of success for the type of disorder detected. If the electrical activity is not recognizable by the software algorithm or if a specific treatment area is not distinguishable, then the device can offer the clinician the option of administering a default, general treatment to more than one area and possibly a series of treatments to all areas.

The appropriate electrodes (the same or different from the sensing electrodes) can then be electronically switched into the treatment delivery circuit and connected to one or more programmable power supplies.

The optimized voltage waveform calculated in step D can then be applied to the appropriate electrodes. Before application of voltage to the electrodes, a summary of the results of step A through step E can be displayed and the clinician can be offered the option of continuing or discontinuing the treatment.

All pertinent data and information gathered and generated during steps A through F can be stored electronically and/or printed out for the patient's records and for improving the treatment algorithm. With an appropriate rating scheme for patient outcomes, the software and its associated databases may be improved using standard software evolutionary techniques.

Figure 4A:
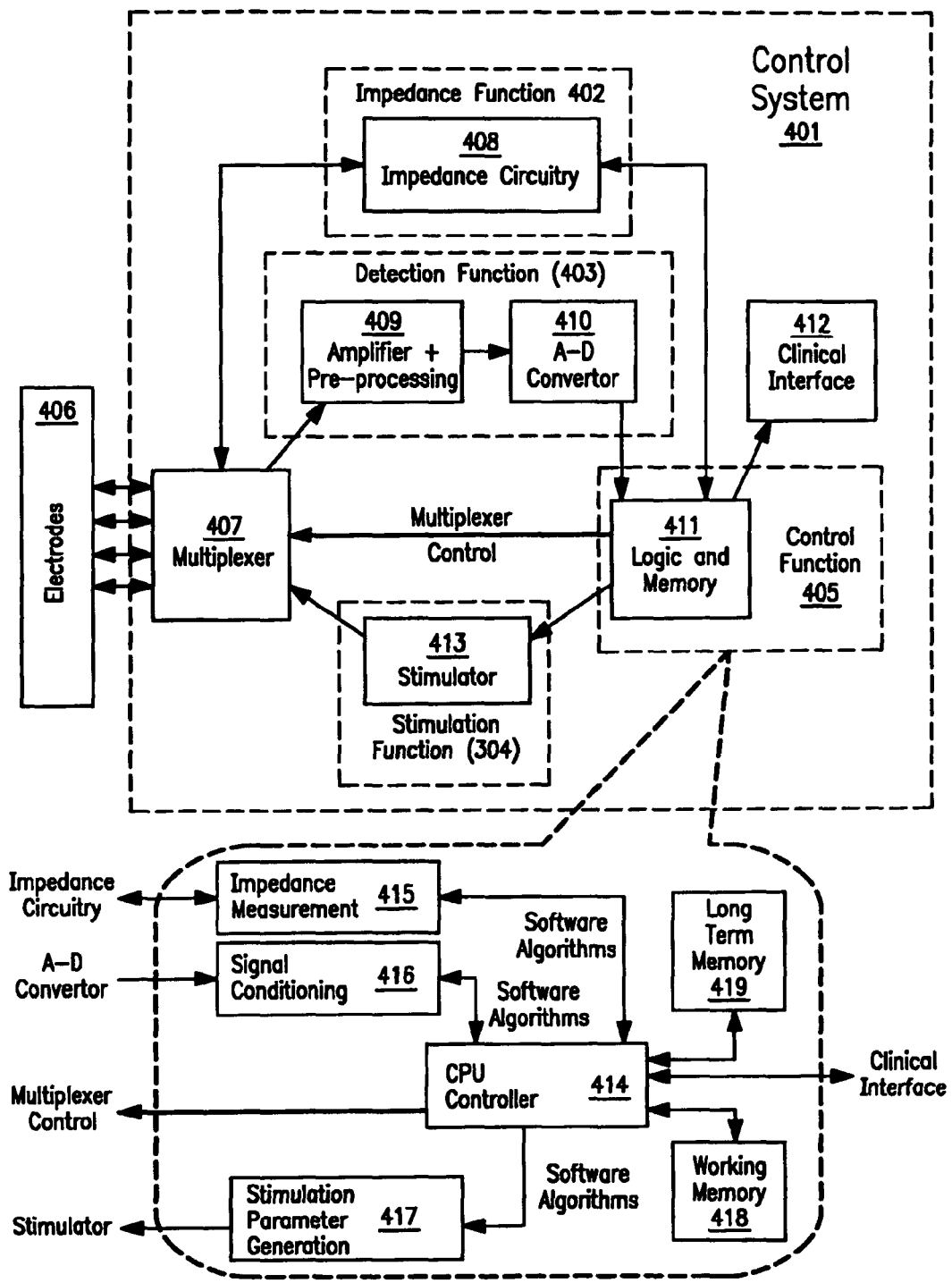
FIG. 4A schematically illustrates the electronic control system, according to an 15 embodiment of the present invention.
Figure 4B:
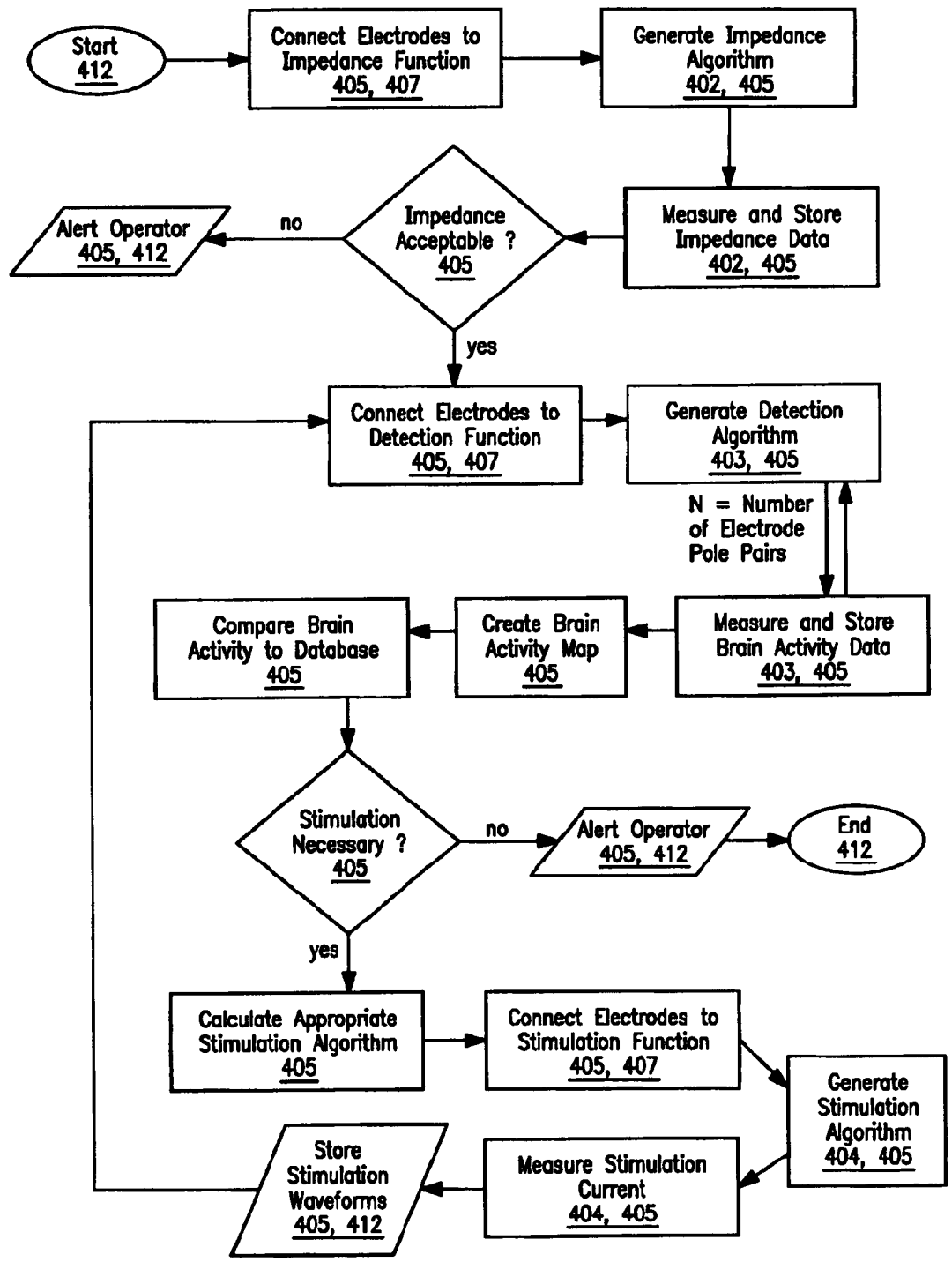
FIG. 4B schematically illustrates an algorithm of the control system, according to an embodiment of the present invention.

In one embodiment of the present invention, as illustrated in FIGS. 4A and 4B, the treatment system 400 comprises the electrode(s) 406 connected to a control system 401. The control system 401 performs a sequence of measurements, calculations and power delivery using the electrodes 406 as both sensors and as power delivery circuit components. The electrodes 406 are in electrical contact with the patient and may be implanted, adhered to the scalp or mounted in a helmet or cap type device. If electrodes 406 are attached individually, their position on the head is entered via the clinical interface 412. This data can be determined using true position or other mechanical inspection devices. The electrodes 406 are connected to the treatment system via a multiplexing network 407. The multiplexer 407 can be configured to connect the electrode(s) 406 to any of the three functional circuit groups. These functional circuit groups are the Impedance Group 402, Detection Group 403, and Stimulation Group 404. Control of these groups is performed by the Control Group 405.

The treatment sequence begins with a command via the clinical interface 412. The control function 405 initiates a sequence of voltages to be individually applied to each electrode 406, by the impedance circuitry 408 via the multiplexer 407. The impedance circuitry 408 then measures the current to each electrode 406 pole and sends the measured value to the control function 405. This sequence is repeated for each possible combination of electrode 406 poles. The logic and memory 411 component processes the information and determines the individual impedance of each possible combination of electrode 406 poles. This information is stored and is used to determine the necessary voltages to be applied during the treatment.

The control function 405 then activates the detection function 403, and the electrodes 406 are connected by the multiplexer 407 to the amplifier 409 in the detection function 403. The electrical activity is monitored and compared to a data base of normal and/or abnormal waveforms by the control function 405. When an abnormal waveform is detected, its relative signal strength in each electrode 406 is measured. Combining this information with the electrode 406 location data from above allows the control function 405 to determine the location of the abnormal electrical activity. From this information, the control function 405 can calculate the optimum electrode 406 pole pairs to be energized to deliver treatment to the targeted area. The abnormal electrical activity's specific waveform type can be associated with a preferred treatment waveform, which can then be selected by the control function 405. Using the information processed during the impedance determination, the amplitude of the selected treatment waveform can be calculated such that the desired current can be delivered to the targeted area.

Once a treatment waveform, amplitude, and the appropriate electrode 406 poles have been selected, the control function 405 can connect the selected electrode 406 poles to the stimulator 413 in the stimulation function 404 via the multiplexer 407. The control function 405 can then signal the stimulator 413 to deliver the therapeutic current waveform to the targeted area.

The control function 405 and clinical interface 412 may comprise a personal computer or laptop computer with appropriate software.

In one embodiment of the present invention, the subgaleally located stimulation device comprises a battery power unit and a control unit that comprises a receiver unit. The receiver unit receives wireless signals from an external sending unit to trigger the control unit for stimulation.

In one embodiment of the present invention, an operator can program the control unit via wireless and/or radio-controlled means.

In one embodiment of the present invention, the battery power unit can be re-charged by alternating magnetic fields.

In one embodiment of the present invention, the patient can turn on and off the device manually, via a wireless and/or radio controlled means, or by swiping a magnet over the control unit or the device.

The switching circuit for driving one or more discrete electrode arrays has selectable multiple driving stimulation parameter modes. The circuit has a control unit for outputting a mode-switching signal and a data driving unit connecting with the control unit for providing a data signal.

Epicranial Implanted Electrodes

For cortical stimulation, epicranial located targeting electrodes appear most beneficial. Epicranial implanted electrodes can be used to electrically monitor portions or all of the brain or nerve structures, stimulate portions or all of the brain or nerve structures, or any combination thereof. For the ease of the discussion, the targeting electrodes as shown in this section 6 are shown as cross-sections of discrete array electrodes. However, the same methods described herein can be applied to pure ring type electrodes.

FIG. 5A1 and FIG. 5A2 illustrate a human head 514 (without hair for better illustration) in which an incision 515 is made through the scalp, and a sheet of electrodes 516 is pushed under or into the scalp. The incision is made in such a way that the sheet of electrodes 516 can be located immediately on top of the spot under which the brain region is located and which shall be stimulated or electrically monitored.

In another embodiment of the present invention, the targeting electrodes are implanted by opening the scalp 519 and placing a flexible sheet of electrodes 517, as shown in FIG. 5A1 and FIG. 5A2. The opening incision 519 is made in such a way that the sheet of electrodes 517 can be located immediately on top of the spot under which the brain region is located and which shall be stimulated or electrically monitored.

In general, the sheet of electrodes comprises one or more electrodes. The substrate material comprises flexible or rigid but biocompatible material, such as silicone, polyethylene (PE), polypropylene (PP), polyurethane (PU), latex, or any other biocompatible plastic or rubber. The electrodes, which are printed, evaporated, or mounted in any other form on top of the substrate, comprise biocompatible material. Metals used for electrodes or wiring comprise material compatible with magnetic resonance imaging (MRI), such as titanium alloys that contain 2% to 7% aluminum and 2% to 5% vanadium (especially ASTM grade 5 and 9), being un-magnetic and comprising a controlled image artifact (MR image distortion is close to the one of water). When the sheet is placed correctly, the incision will be closed.

In one embodiment of the present invention, the battery pack and control electronics are also implanted beneath the skin. In one embodiment of the present invention, the battery pack and control electronics are also implanted beneath the skin but further away from the incision, such as under the collarbone. In one embodiment of the present invention, the battery pack and control electronics are not implanted, but connected by wires that pass through the skin. In one embodiment of the present invention, the power and the control signals are inductively transferred from a non-invasive unit to the implanted electrode system. In one embodiment of the present invention, only the control signals are inductively transferred from a non-invasive unit to the implanted electrode system, but the electrode system comprises an implanted battery unit. Any part of the cranium or the entire cranium can be covered with subgaleally implanted electrodes.

Figure 5B:
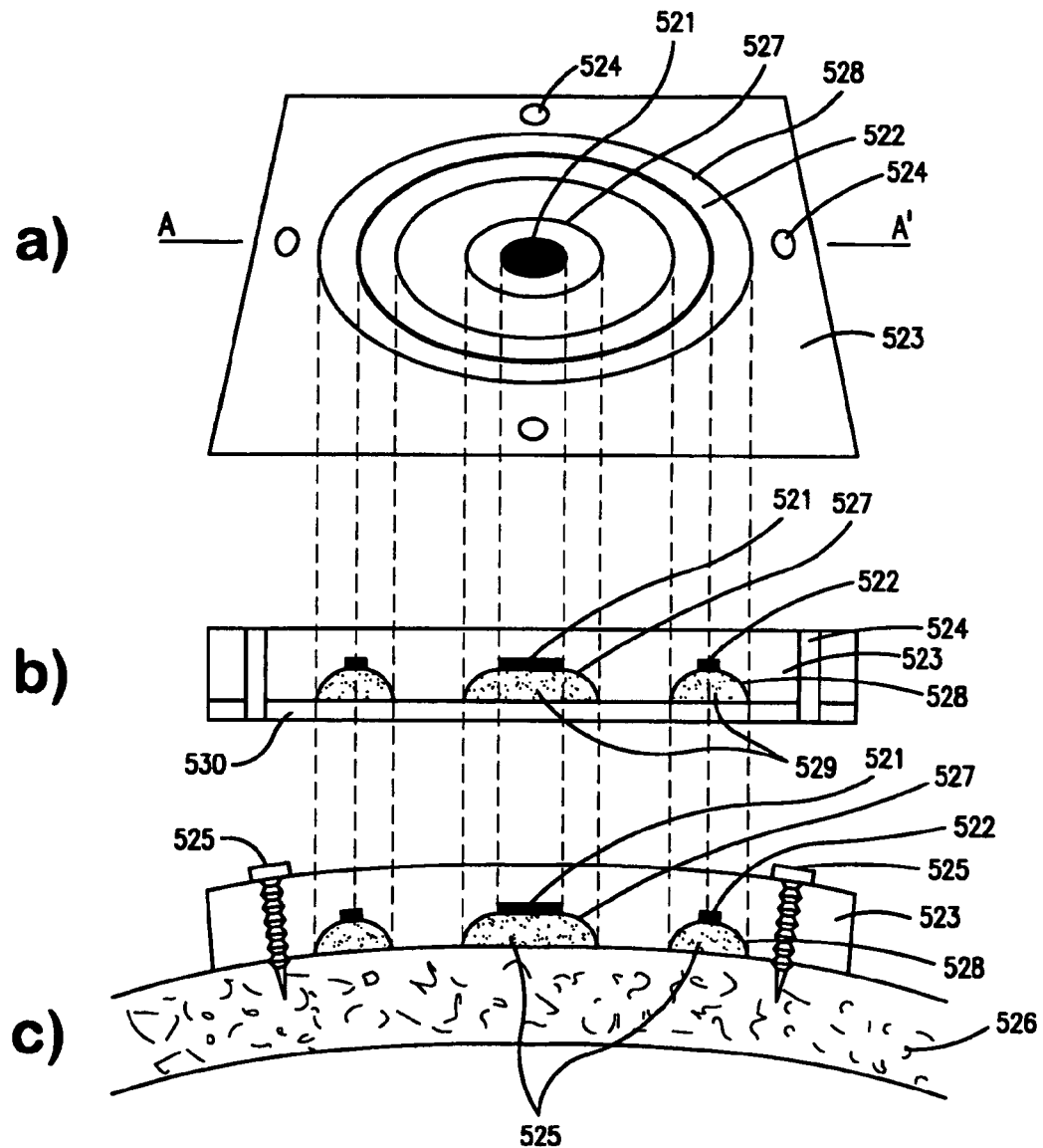
FIG. 5B schematically illustrates an implantable disc-ring electrode which is to be fixed on the skull via screws, according to an embodiment of the present invention.

FIG. 5B illustrates an implantable electrode with one center disc 521 and one ring electrode 522 surrounding the disc 521, which could be a Laplace electrode or a concentric ring electrode. FIG. 5Ba is a three dimensional top view, and FIG. 5Bb and FIG. 5Bc are cross sectional views through the axis AA'. Dimensions of structures in the figures are altered for illustrative purposes and thus are not as they would appear for the actual device. The number of electrodes is selected to be 2 for simplicity purposes; any other number would be feasible. Electrodes 521 and 522 comprise biocompatible conductive material and are mounted to the substrate 523. In one embodiment of the present invention, the electrodes 521 and 522 are evaporated on the substrate 523. In one embodiment of the present invention, the electrodes 521 and 522 are sputtered on the substrate 523. In one embodiment of the present invention, the electrodes 521 and 522 are etched from a metal layer on top of the substrate 543.

The substrate 523 comprises flexible and biocompatible material, and comprises holes 524 through which biocompatible screws 525 can be inserted to fix the substrate 523 onto the cranium 526 or skull 526. Alternatively, the screws 525 may be screwed through the substrate, without the use of holes 524, directly into the skull 526. Alternatively, the substrate 523 could be taped onto the skull 526 or not fixed to the skull 526 at all.

In one embodiment of the present invention, as illustrated in the cross-sections of FIGS. 5Bb and 5Bc, the electrodes 521 and 522 are embedded in trenches 527 and 528, which are a little larger than the electrodes 521 and 522 themselves. The trenches 527 and 528 are filled with conductive paste 529. The paste ensures good electrical contact to the skull 526, which itself is a rather poor electrical conductor. The purpose of the arrangement of electrodes with said trenches is to ensure that the electrodes do not shunt too much. Screws 525 fix the substrate structure onto the cranium to fix the general location of the device and to push the substrate 523 with electrodes and paste to the curved cranium, see FIG. 5Bc. When delivered to the physician, the device comprises a cover foil 530, which is removed and disposed in order to implant the device.

Figure 5C:
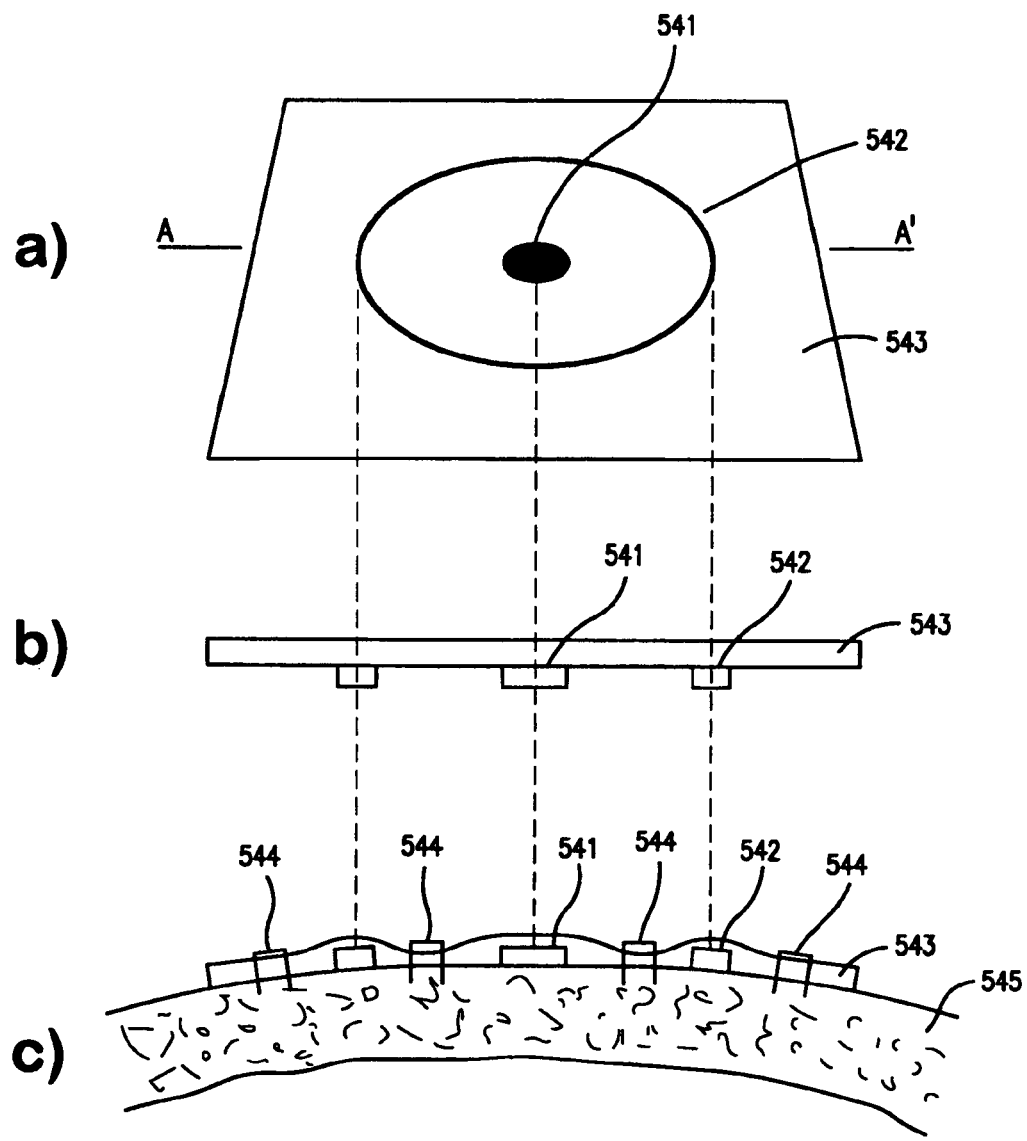
FIG. 5C schematically illustrates an implantable disc-ring electrode, according to an embodiment of the present invention; 25

FIG. 5C illustrates an implantable electrode with one center disc 541 and one ring electrode 542 surrounding the disc 541, which could be a Laplace electrode or a concentric ring electrode. FIG. 5Ca is a three-dimensional top view and FIG. 5Cb and FIG. 5Cc are cross-sectional views through the axis AA'. Dimensions of structures in the figures are not as they would appear for the actual device but are altered for illustrative purpose. The number of electrodes is selected to be two only for simplicity purposes, as any other number would be feasible. Electrodes 541 and 542 are fabricated from biocompatible conductive material and are mounted to the substrate 543. The substrate 543 is fabricated from flexible and biocompatible material.

In this embodiment of the present invention, as illustrated in the cross-sections of FIG. 5Cb and FIG. 5Cc, the electrodes 541 and 542 are on top of the substrate 543. In one embodiment of the present invention, the electrodes 541 and 542 are evaporated on the substrate 543. In one embodiment of the present invention, the electrodes 541 and 542 are sputtered on the substrate 543. In one embodiment of the present invention, the electrodes 541 and 542 are etched from a metal layer on top of the substrate 543. In this embodiment of the present invention, the substrate 543 is stapled via stable needles 544 onto the cranium or skull 545. Alternatively, the substrate 543 is taped onto the skull 545, or not fixed to the skull 545 at all. Conductive paste may be used to enhance the electrical contact. When delivered to the physician, the device may comprise a cover foil, which is removed and disposed in order to implant the device.

Figure 5D:
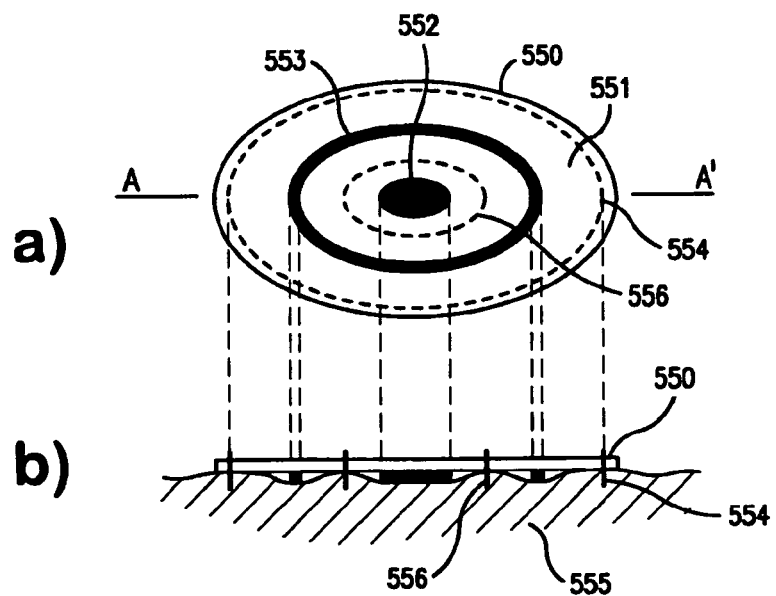
FIG. 5D schematically illustrates an implantable disc-ring electrode which is to be stitched or stapled to tissue, according to an embodiment of the present invention.

FIG. 5Da illustrates an embodiment of the present invention in which a 3-dimensional view of an implantable electrode system 550 that comprises a flexible biocompatible substrate 551 on which one circular center electrode 552 and one concentric ring electrode 553 are fixed. The substrate 551 is constructed in such a way that one can stitch through the material to stitch the substrate onto tissue of any organ. Lines 554 and 556 represent the stitching sutures in the substrate 551. Alternatively, the electrode system 550 is stapled or glued onto an organ or in a tissue.

FIG. 5Db illustrates a cross-sectional view along the AA' axis of FIG. 5Da. The system 550 is stitched via suture 554 onto the tissue 555. In this particular case, the sutures are stitched through the substrate 551 between the disc 552 and the ring 553 and outside the ring 553. In order to better connect the electrodes 552 and 553 to the tissue 555, the sutures preferably pass through the electrodes 552 and 553.

Figure 5E:
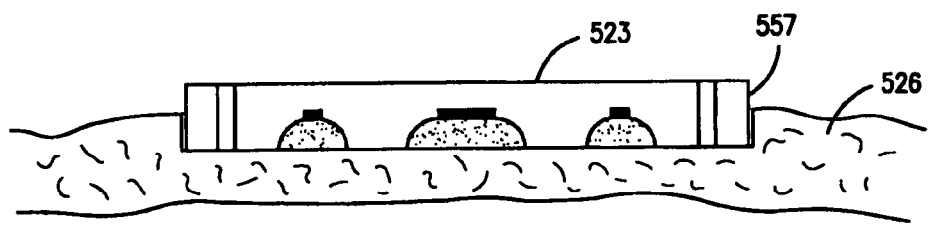
FIG. 5E schematically illustrates a ring electrode system embedded in the cranium bone, according to an embodiment of the present invention.

FIG. 5E illustrates the same ring electrode system 523 as in FIG. 5B, with the exception that here the ring electrode system 523 is embedded into the cranium bone 526 of the skull. The embedding hole 557 is created by drilling or chiseling the bone 526.

The type of electrodes as shown in this embodiment of the present invention do not necessarily have to be ring, concentric ring or Laplace electrodes, but could be of any type described in this application. The implanted electrodes can be used for sensing, stimulation, or a combination thereof.

In one embodiment of the present invention, the system comprises a seizure detection algorithm or seizure onset detection algorithm that controls the stimulation.

In one embodiment of the present invention, the stimulation by implanted electrodes is performed in combination with drugs to enhance the therapeutic effect.

In one embodiment of the present invention, an array of electrodes sense the focus or location of the seizure, and an algorithm is utilized to determine the optimal subset of electrodes to stimulate only said focal region.

In one embodiment of the present invention, sensing and stimulating electrodes can be the same, different from each other, or any combination thereof.

In one embodiment of the present invention, sensing, detecting of the seizure focus, and stimulating is performed successively to follow a moving or in time and space varying seizure focus.

In one embodiment of the present invention, the electrodes stimulate jointly utilizing a phased array method.

In one embodiment of the present invention, the implanted electrodes stimulate jointly utilizing a phased array method.

In one embodiment of the present invention, the implanted electrodes are utilized for cardiac stimulation, especially for defibrillation.

In one embodiment of the present invention, the implanted electrodes are utilized for obesity treatment or appetite suppression.

In one embodiment of the present invention, the implanted electrodes are utilized for pain treatment or pain management, especially for spinal nerve stimulation.

In one embodiment of the present invention, the implanted electrodes are utilized for stimulation of peripheral nerves.

In one embodiment of the present invention, the implanted electrodes are utilized for muscle stimulation and muscle build-up or muscle training.

In one embodiment of the present invention, the implanted electrodes are utilized for the treatment of paralysis. 30

The typical stimulation signals used in the implantable device of the present invention are preferably biphasic (that is, with equal energy positive and negative of ground), with a typical frequency in the range of from about 10 Hz to about 250 Hz, although frequencies in the range of from about 0.1 Hz to about 2500 Hz may be effective. The typical width of the biphasic pulse is preferably between about 50 μsec (microseconds) and about 500 μsec, although pulse widths of about 10 μsec to about 10 sec (seconds) may be effective for a particular patient. The pulse width of the positive and negative phases may be of different durations and/or magnitudes. Typically, voltage is applied in the range of from about 30 V (volts) to about 100 V, and current amplitudes in the range of from about 5.0 mA (milliamperes) to about 50 mA. However, it may be beneficial using magnitudes above 2000 V if the skin-to-electrode impedance is above 40,000 ohms. Stimulation is applied for a duration of from about 15 sec to 30 min (minutes), preferably, from about 30 sec to about 5 min.

If ring electrodes are used, electrodes with 1 center disc and 1 to 10 rings are used, however, typically 1 to 3 rings are used. Generally, the rings are of equal radial distance to each other, but can also be of varying distance. The radial distance is typically between 3 mm and 10 mm, but can also be between 0.3 mm and 30 mm. The rings in general are of equal width, but can also be of varying width. The width of the rings is typically 1 mm to 3 mm, but can also be between 0.1 mm and 10 mm. The center disc electrode typically has a radius between 2 mm and 4 mm, but can also be up to 10 mm. Some ring electrodes may not have a center disc electrode. In general, ring electrodes are concentric, but may also be elliptical. Typical ratio of the two elliptic axes is up to 2, but it can go up to 10. The thicknesses of the electrodes in a ring electrode are typically about equal, but it can also vary. Typically, thicknesses are between 0.001 mm and 0.01 mm, but can range between 0.0001 mm and 1.0 mm. The electrodes are typically fabricated from a metal, which such as gold, stainless steel, platinum, copper, copper alloys, titanium, or titanium alloys.

The number of Laplace, concentric ring, or ring type electrodes in a typical implantable device is typically between 1 and 12, but can also be between 1 and 100. Any neurological disease can be treated with the device of the present invention. The device can be used purely for sensing, such as EEG. The device can be implanted temporarily or permanently. The device can be implanted sub-cranially.

The device of the present invention comprises a detection algorithm that detects seizures from the sensed signals. For moderate starting seizure signals, moderate stimulation is administered. If the seizure evolves, more intense stimulation is administered, which comprises more pulses or more amplitude or a combination of both. If the detected seizure signals decrease, then less stimulation is administered.

Figure 6A:
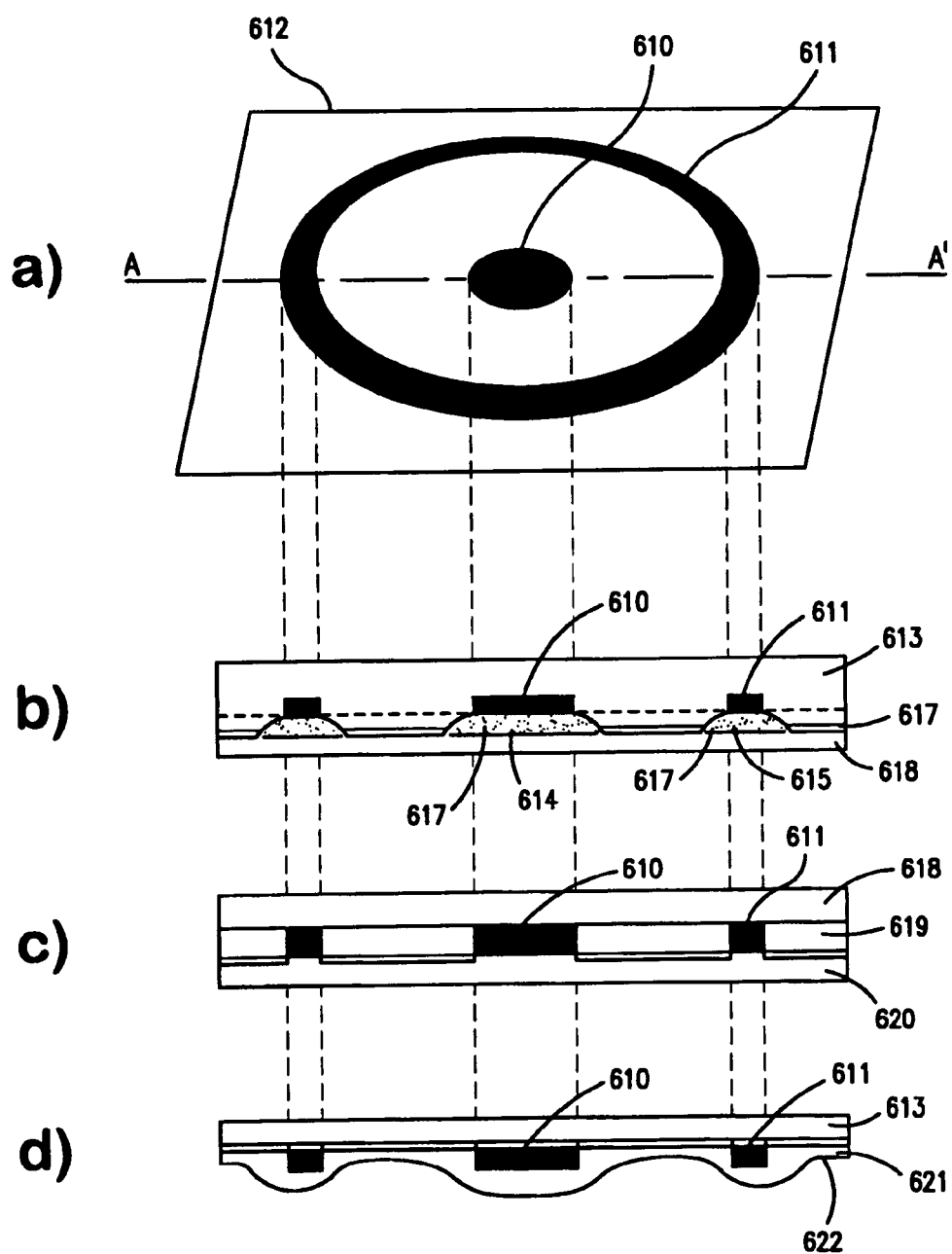
FIG. 6A schematically illustrates disc-ring electrode configurations of an electrode which can be taped onto the skin, according to an embodiment of the present invention.

Determining the correct location for positioning the electrodes can be accomplished using Magnetic Resonance Imaging (MRI), functional MRI (fMRI), Diffusion Weighted MRI (DWI), Diffusion Tensor MRI (DTI), x-ray fluoroscopy, Computer Tomography (CT), Ultrasound (US), Single Photon Emission Computed Tomography (SPECT), or Positron Emission Tomography (PET). Electrode Plaster Patches In one embodiment of the present invention, stimulating and sensing electrodes are taped onto the skin in the form of a plaster. Although ring type Laplace electrodes are disclosed in this section of the present invention, any type of targeted electrode may be utilized for the same purpose. FIG. 6Aa illustrates, in a 3-dimensional view, a plaster 612 that can be taped onto the skin with a concentric ring electrode comprising of one circular center disc electrode 610 and one concentric ring electrode 611. However, this embodiment is not limited to the number of rings shown in the figure. FIG. 6Ab, FIG. 6Ac and FIG. 6Ad illustrate cross-sectional views along axis AA' of three different embodiments through the plaster 612.

In FIG. 6Ab, the electrodes 610 and 611 are fixed on to the flexible substrate 613. The electrodes 610 and 611 are located in trenches 614 and 615, which are further filled with electrical conductive paste 617. On top of the substrate 613 is a layer 617 of tape or glue with which the plaster can be taped onto the skin of the patient after a covering foil 618 has been removed. Having the conductive paste only in the trench ensures minimal electrical shunting between the electrodes 610 and 611.

FIG. 6Ac illustrates a different embodiment of the plaster 612 wherein the electrodes are embedded in the flexible substrates 618 and 619. Substrate 619 can be taped or glued onto the human skin. Cover foil 620 protects the taping substrate 619 and has to be removed prior to taping this plaster onto tissue.

FIG. 6Ad illustrates, in cross-sectional view, a flexible substrate 613 on which the electrodes 610 and 611 are fixed. A taping layer 621 is printed between the electrode structures 610 and 611, and a cover layer 622 protects the structure but must be removed prior to using the device.

Conductive paste for structures, as shown in FIG. 6Ac and FIG. 6Ad, may be smeared on to the electrodes prior to taping the plaster. Alternatively, conductive paste may be inserted into the structure as an extra layer (not shown in figure).

Electrodes can be mounted onto the substrate via evaporation through a mask, evaporation and structural etching, sputtering, chemical vapor deposition, printing, or painting. The plasters suitable for use herein can be taped onto or into skin, bone, hair, and mucosa or teeth tissue.

Figure 6B:
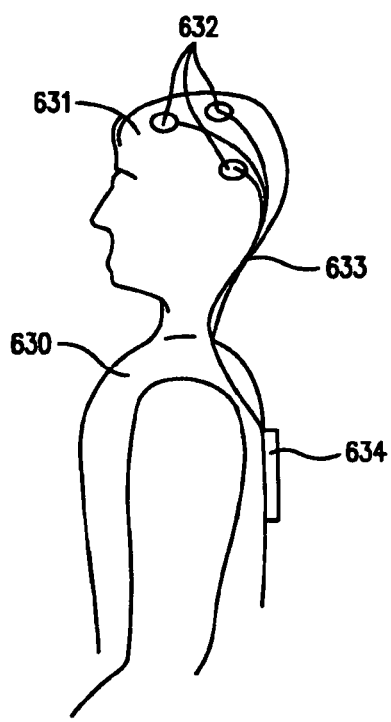
FIG. 6B schematically illustrates a human body with attached electrodes, leads and control unit, according to an embodiment of the present invention. 5

FIG. 6B illustrates a patient wearing a sensing and stimulation system. In this embodiment of the present invention, sensing and stimulation electrodes 632 are taped onto the skin of the head 631 and wires 633 connect each electrode with the control unit 634 that the patient wears anywhere on his/her body 630.

Laplace electrodes or multi-concentric ring electrodes with or without a center disc have a greater targeting stimulation characteristic than conventional disc electrodes. A system of targeted electrodes is beneficial in sensing and/or stimulating the neuro or nervous tissue.

In one embodiment of the present invention, non-invasive targeted electrodes may be used to verify the effectiveness of stimulation for a neurological illness. There are stimulation systems on the market or in research which require at least the electrodes or the entire system to be implanted. However, implanting electrodes is a high barrier for patients, especially if the implantation requires opening the skull. To overcome this barrier, noninvasive targeted electrodes can be used temporarily or permanently to stimulate neurological or nervous structures of the brain, spine, or anywhere else in the body. Non-invasive targeted stimulation can be used if a particular symptom or disease of a particular patient responds favorably to stimulation, and which is them used to make the determination of the feasibility of a permanent implantable stimulation device.

In one embodiment of the present invention, non-invasive targeted electrodes may be used temporarily to lower the symptoms of neurological illnesses. Brodmann area (BA25) is an area in the cerebral cortex of the brain that has been proposed to be involved in depression. One or more non-invasive targeted electrodes can be placed on the scalp to stimulate area during depressive episodes. In another embodiment of the present invention, the same method is used for treating temporary migraine attacks. In another embodiment of the present invention, non-invasive targeted electrodes are placed on locations of the scalp, which are on top of motor regions to stimulate these for stroke rehabilitation.

In one embodiment of the present invention, non-invasive targeted electrodes are used to treat chronic epilepsy. About one third of epilepsy patients do not respond to medication. Some epileptic patients refuse to take medication due to their side effect. Some epilepsy patients have seizures only during certain periods (wake up phase, monthly period, etc.), while others have cluster seizures or auras. Epilepsy patients could tape the electrodes to the skin areas that their physicians believe to be closest to the focal brain area from which the seizure is to expected to start. The system can remain in sensing mode and be turned to stimulation mode when desired.

In one embodiment of the present invention, the system comprises a seizure detection algorithm or a seizure onset detection algorithm which controls the stimulation.

In one embodiment of the present invention, the stimulation by non-invasive targeted electrodes is performed in combination with drugs to enhance the therapeutic effect.

In one embodiment of the present invention, an array of non-invasive electrodes sense the focus or location of the seizure, and an algorithm is used to determine the optimal subset of non-invasive targeted electrodes to stimulate only said focal region.

In one embodiment of the present invention, sensing and stimulating electrodes are the same, but can be different from each other, or a combination hereof.

In one embodiment of the present invention, sensing, detecting of the seizure focus and stimulating is performed successively to follow a moving or in time and space varying seizure focus.

In one embodiment of the present invention, the non-invasive targeted electrodes stimulate jointly utilizing a phased array method.

In one embodiment of the present invention, non-invasive targeted electrodes are utilized for cardiac stimulation, especially for defibrillation.

In one embodiment of the present invention, non-invasive targeted electrodes are utilized for obesity treatment or appetite suppression.

In one embodiment of the present invention, non-invasive targeted electrodes are utilized for pain treatment or pain management, especially for spinal nerve stimulation.

In one embodiment of the present invention, non-invasive targeted electrodes are utilized for stimulation of peripheral nerves.

In one embodiment of the present invention, non-invasive targeted electrodes are utilized for muscle stimulation and muscle build-up or muscle training.

In one embodiment of the present invention, non-invasive targeted electrodes are utilized for the treatment of paralysis.

In one embodiment of the present invention, non-invasive targeted electrodes are utilized for the treatment of diabetic neuropathy.

In one embodiment of the present invention, non-invasive targeted electrodes are utilized for sphincter stimulation in incontinence treatment.

In one embodiment of the present invention, non-invasive targeted electrodes are utilized for stimulation of the sympathetic nerve system.

In one embodiment of the present invention, non-invasive targeted electrodes are utilized for stimulation of the parasympathetic nerve system.

The typical stimulation signals used in this plaster device are preferably biphasic (that is, with equal energy positive and negative of ground), with a typical frequency in the range of from about 10 Hz (Hertz) to about 250 Hz, although frequencies in the range of from about 0.1 Hz to about 2500 Hz may be effective. The typical width of the biphasic pulse is preferably between about 50 μsec and about 500 μsec, although pulse widths of about 10 μsec to about 10 sec may be effective for a particular patient. The pulse width of the positive and negative phases may be of different durations and/or magnitudes. Typically, voltage is applied in the range of from about 30 V to about 100 V, and current amplitudes in the range of from about 5.0 mA to about 50 mA. However, it may be beneficial using magnitudes above 2000 V if the skin-to-electrode impedance is above 40,000 ohms. Stimulation is applied for a duration of from about 15 sec to 30 min, preferably, from about 30 sec to about 5 min.

If ring electrodes are utilized, electrodes with 1 center disc and 1 to 10 rings are used, however, typically 1 to 3 rings are used. The rings are generally of equal radial distance to each other but can also be of varying distance. The radial distance is typically between about 3 mm and about 10 mm, but can be between 0.3 mm and 30 mm. The rings in general are of equal width, but can also be of varying width. The width of the rings is typically 1 mm to 3 mm, but also can be between 0.1 mm to 10 mm. The center disc electrode has typically a radius between 2 mm and 4 mm, but can also be up to 10 mm. Some ring electrodes may not have a center disc electrode. In general, ring electrodes are concentric but may also be elliptical. Typical ratio of the two elliptic axes is up to 2, but it can go up to 10. The thicknesses of the electrodes in a ring electrode are typically about equal, but they can vary. Typically, thicknesses are between 0.001 mm and 0.01 mm, but can range between 0.0001 mm and 1.0 mm. The metals typically used for the electrodes are gold, stainless steel, platinum, copper, copper alloys, titanium, or titanium alloys.

The number of Laplace, concentric ring, or ring type electrodes in a plaster device is typically between 1 and 6, but can also be between 1 and 100. Any neurological disease can be treated with the device of the present invention. The device can be used purely for sensing, such as EEG. The device can be worn by the patient temporarily or permanently.

The device of the present invention comprises a detection algorithm that detects seizures from the sensed signals. For moderate starting seizure signals, moderate stimulation is administered. If the seizure evolves, more intense stimulation is administered, which comprises more pulses or more amplitude or a combination of both. If the detected seizure signals decrease, then less stimulation is administered.

Determining the correct location for positioning the electrodes can be accomplished using Magnetic Resonance Imaging (MRI), functional MRI (fMRI), Diffusion Weighted MRI (DWI), Diffusion Tensor MRI (DTI), x-ray fluoroscopy, Computer Tomography (CT), Ultrasound (US), Single Photon Emission Computed Tomography (SPECT), or Positron Emission Tomography (PET).

Acute Seizure Control Device

For acute seizure control of epilepsy, a cap or helmet device is utilized to treat a seizing patient by placing said device on the patient's head. Although ring type Laplace electrodes are disclosed in this section of the present invention, any type of targeted electrode may be utilized for the same purpose.

FIG. 7 illustrates a patient's head 701 in side view, and from the top-front. The cap or helmet 702 comprises a finger-like structure 703 which comprises a mechanically flexible material. Similar to a flat held human hand that can grip different size balls when fingers are bent inwards (adduction), the finger-like structure 703 of the helmet 702 can circumference different head sizes when finger-like structure 703 is flexed inwards. A strap mechanism 704 holds the finger-like structure 703 of the helmet 702 in place. Not shown here is a further strap mechanism around the chin to hold the helmet 702 on the head. The electrodes for sensing and/or stimulation are not shown in the figure, although they are located on the inside surface of the helmet device 702 facing the head 701. The strap mechanism will hold the targeted or conventional electrodes in place. The location of the electrodes on specific sites around the head does not appear to affect the efficiency of the device. More importantly, the electrodes do not change their position between the sensing and stimulation mode of the device.

The stimulation is more effective at lower impedance levels of the contact between the electrodes and the skin and/or through the hair. In general, electro conductive paste is used in between the electrodes and the skin. To assure good contact between the electrodes and the patient's head, the electrodes are pushed by force onto the skin. In one embodiment of the present invention, the force is caused by mechanical springs. In another embodiment, the force is caused by compressed rubber. In another embodiment, the force is caused by pneumatically means. In another embodiment, the force is caused by hydraulic means.

In one embodiment of the present invention, the electronic control unit and the battery unit are integrated into the helmet 702. In another embodiment, the electronic control unit is integrated into the helmet 702 but the battery unit is connected via cables to an extra hand-held unit. In another embodiment, the electronic control unit and the battery unit are separated from the helmet 702 in a mobile or hand-held unit. In another embodiment, the battery unit is constantly powered when not is use.

In one embodiment of the present invention, some electrodes are used for sensing and some are used for stimulation, while some are used for successively sensing and stimulation, or any combination thereof. In one embodiment of the present invention, the device is changed successively from sense and detection mode to a stimulation mode, and will stop if no further seizure activity is detected. In one embodiment of the present invention, the magnitude of the seizure detected is used to control the delivered stimulation parameters. In one embodiment of the present invention, the detected electromyographic signals are used to locate the focal area of the seizure, and an algorithm determines from which electrodes to stimulate most effectively. In one embodiment of the present invention, the targeted or conventional electrodes are physically moved, manually or automatically, to different positions around the head.

The typical stimulation signals used in this acute seizure device are preferably biphasic (that is, with equal energy positive and negative of ground), with a typical frequency in the range of from about 10 Hz to about 250 Hz, although frequencies in the range of from about 0.1 Hz to about 2500 Hz may be effective. The typical width of the biphasic pulse is preferably between about 50 μsec and about 500 μsec, although pulse widths of about 10 μsec to about 10 sec may be effective for a particular patient. The pulse width of the positive and negative phases may be of different durations and/or magnitudes. Typically, voltage is applied in the range of from about 30 V to about 100 V, and current amplitudes in the range of from about 5.0 mA to about 50 mA. However, it may be beneficial to use magnitudes above 2000 V if the skin-to-electrode impedance is above 40,000 ohms. Stimulation is applied for a duration of from about 15 sec to about 30 min, preferably, from about 30 sec to about 5 min.

If embodiments in which ring electrodes are utilized, electrodes with 1 center disc and 1 to 10 rings are used, however, 1 to 3 rings are typically used. Generally, the rings are of equal radial distance to each other, but can also be of varying distance. The radial distance is typically between 3 mm and 10 mm, but can also be between 0.3 mm and 30 mm. Generally, the rings are of equal width, but can also be of varying width. The width of the rings is typically 1 mm to 3 mm, but can also be between 0.1 mm to 10 mm. The center disc electrode typically has a radius between 2 mm and 4 mm, but it can also be up to 10 mm. Some ring electrodes may not have a center disc electrode. In general, ring electrodes are concentric, but they may also be elliptical. Typical ratio of two elliptic axes is up to 2, but it can go up to 10. The thicknesses of the electrodes in a ring electrode are typically about equal, but they can also vary. Typically, thicknesses are between 0.001 mm and 0.01 mm, but they can range between 0.0001 mm and 1.0 mm. Metals typically used for the electrodes are gold, stainless steel, platinum, copper, copper alloys, titanium, or titanium alloys.

The number of Laplace, concentric ring, or ring type electrodes in a typical acute seizure control device is typically between 6 and 22, but can be between 1 and 100. Any neurological disease can be treated with the present device. The device can be used purely for sensing, such as EEG. The device can be worn temporarily or permanently.

Medical Care

Currently, the standard treatment of neurological diseases, such as epilepsy, is to start with a couple of drugs. If medication does not treat the disease properly, then electrical stimulation or even brain surgery is considered. With the stimulation techniques of the present invention, the standard of care may change. Prior to introducing a stimulation implant into the brain, one may wish to test if a particular patient is adaptable to electrical stimulation by first taping electrodes on the scalp of the patient for a while, and then implanting the electrodes subgaleally, and then possibly implanting the electrodes subcranially.

As noted above, the present invention is applicable to devices and methods for the electrical stimulation treatment of neurological and nervous disorders. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

Figure 8:
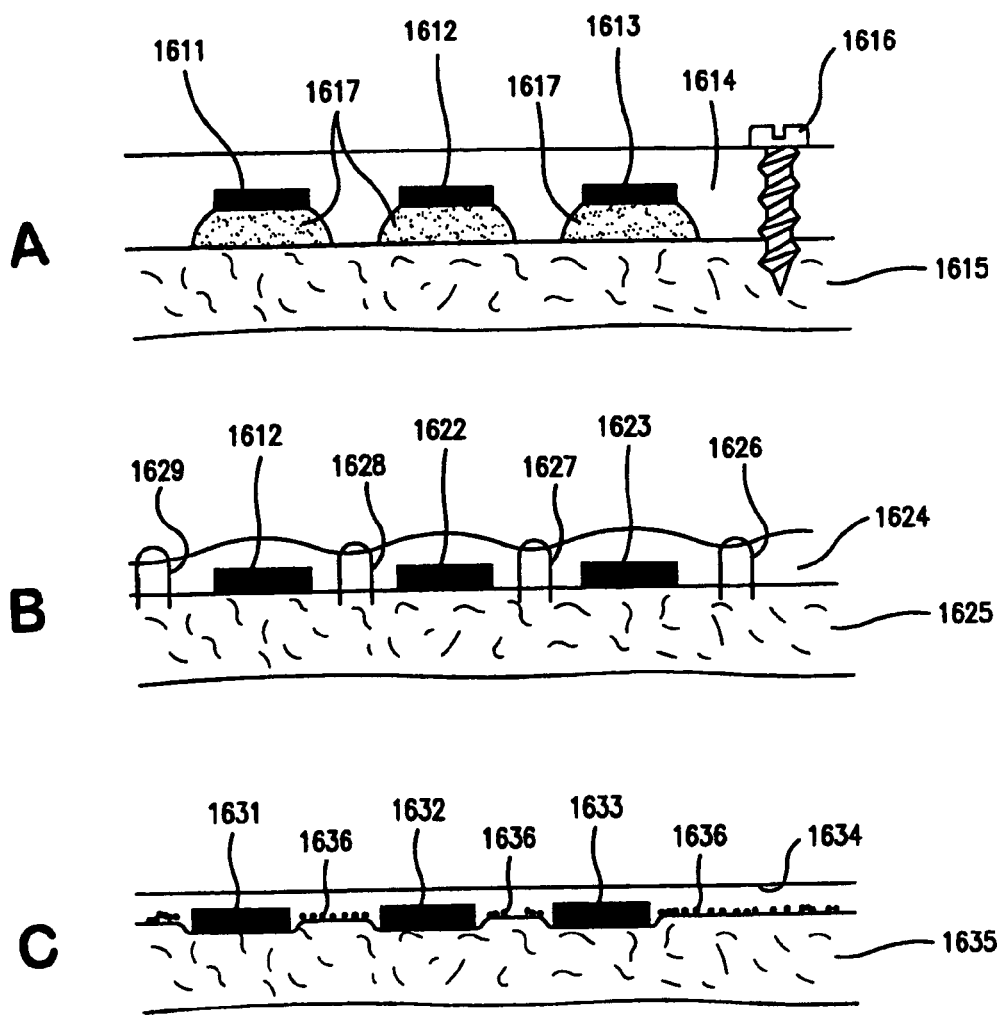
FIG. 8A-8C schematically illustrate cross-sections of various methods to fix targeting electrodes onto the skull (scalp not shown)

FIG. 8 illustrates various methods to fix the targeting electrodes on the skull. The illustrations in FIG. 8 show a cross-section of a portion of a discrete array of electrodes. For ease of viewing, the skull is shown as flat.

FIG. 8A illustrates a cross-section of a portion of an implantable disc-array electrode with discrete electrodes 1611, 1612 and 1613 mounted on a flexible substrate 1614. The substrate 1614 is fixed with bone-screw 1616 onto the skull 1615. Substrate 1614 comprises trenches which are filled with conductive paste 1617.

FIG. 8B illustrates a cross-section of a portion of an implantable discrete-array electrode with discrete electrodes 1621, 1622 and 1623 mounted on a flexible substrate 1624. The substrate 1624 is fixed with staples 1626 to 1629 onto the skull 1625.

FIG. 8C illustrates a cross-section of a portion of an implantable discrete-array electrode with discrete electrodes 1631, 1632 and 1633 mounted on a flexible substrate 1634. The substrate 1634 is fixed with adhesive 1636 onto the skull 1635.

Mounting the electrodes onto the skull can be performed by someone skilled in head and neck surgery or general surgery, and does not require brain surgery.

Substrate Modification

The present invention contemplates stimulation not only to respond to occurrences of abnormal brain activity (responsive therapy), but also to influence, i.e. modify the substrate of brain activity (preventive therapy) to alter the onset of abnormal brain activity, for example. As mentioned herein, it has been shown by Fregini et.al. and Liebetanz et.al. that electrical direct current (DC) stimulation can alter the cortical excitability for seizures. Cathodal DC stimulation—in which the cathode is placed in proximity to the seizure focus—appears to increase the brain's threshold to develop seizures while anodal decreases the threshold. The present invention utilizes the delivery of direct cathodal current for one example of substrate modification in which the electrical excitability of brain tissue is lowered, to prevent or render less frequent, or otherwise modify, epileptic attacks. However, the method of Fregini et al utilizes rather large sponge-like 35 cm² skin surface electrodes connected to wires external to the body which are in turn connected to an electrical stimulator also external to the body in order to deliver current to the brain. Similarly, Liebetanz et al in their rat studies utilize electrodes connected to external wires and an external stimulator in order to deliver current to the brain.

In one embodiment of the present invention substrate modification is achieved with an entirely implanted system consisting of at least one subscalp electrode connected through at least one wire which resides entirely within the body to an electrical stimulator which also resides entirely within the body. This system can be programmed to deliver electrical current on a chronic basis to the brain of a patient over extensive periods of time (months or years) for the purposes of substrate modification without the need to attach external devices to the patient on an ongoing basis. This system is thus suitable for treatment of chronic brain conditions whereas the methods of Fregini and Liebetanz et al are not.

In one embodiment, two or more subscalp electrodes are used to deliver current to the brain and are positioned anatomically on the skull to preferentially deliver current to the desired regions of the brain.

In one embodiment of the present invention, a reference electrode is associated with the container in which the electrical stimulator is located. In one embodiment the electrically conducting outer surface of the container in which the electrical stimulator is located comprises the reference electrode. In these embodiments current is passed through at least one subscalp electrode, positioned to preferentially deliver current to the desired region of the brain, and current returns through the reference electrode.

In one embodiment the electrical stimulator is implanted in the subpectoral region of the body.

In one embodiment at least one subscalp electrode has an area of at least 5 square centimeters.

In one embodiment of the present invention, the subscalp electrodes are used to deliver electrical current on a chronic or ongoing basis for preventive purposes.

In one embodiment of the present invention, the subscalp electrodes deliver this current on a non-triggered basis—that is not in response to abnormal electrical activity of the brain detected within the preceding seconds or minutes.

In one embodiment of the present invention, current is delivered to reduce the susceptibility of the brain to seizure activity.

In one embodiment of the present invention, current is delivered to treat headaches. In another preferred embodiment, current is delivered to treat depression, hyperactivity or mania.

In one embodiment of the present invention, direct current stimulation is delivered. In one embodiment the direct current stimulation is delivered by subpericranial or subgaleal positioned electrodes.

In one embodiment of the present invention, cathodal direct current is delivered.

In one embodiment of the present invention, cathodal direct current is delivered to reduce seizure activity.

In one embodiment of the present invention, cathodal direct current is delivered to treat hyperactivity or mania.

In one embodiment of the present invention, anodal direct current is delivered.

In one embodiment of the present invention, anodal direct current is delivered to treat depression.

In one embodiment of the present invention, cathodal or anodal direct current stimulation is delivered constantly or recurrently in time intervals of constant or changing duration.

In one embodiment of the present invention, constant or recurrent DC or AC stimulation is used from subpericranial or subgaleal positioned electrodes to increase the brain's threshold for seizures while responsive stimulation is used in addition to treat acute epileptic seizure activity.

In one embodiment of the present invention, biphasic or monophasic alternating current (AC) stimulation is delivered constantly or recurrently in time intervals of constant or changing duration.

In one embodiment of the present invention, preventive DC or AC stimulation is performed using intervals of DC current between approximately 1 minute and 60 minutes, preferably between 1 minute and 20 minutes. Duty cycles, defined as the time the DC current is on divided by the time the DC current is off, are between approximately 0.01 and 100.0, preferably 0.1 to 10.0, currents between approximately 0.01 mA and 100 mA, preferably between approximately 0.5 mA and 5 mA, and voltages between approximately 0.1 V and 150 V, preferably between approximately 1 V and 25 V.

In one embodiment of the present invention, preventive DC or AC stimulation is performed in episodes, which may contain a number of intervals.

In one embodiment of the present invention, at least one episode of preventive DC or AC stimulation is performed per day.

One embodiment, utilizes targeting subscalp electrodes capable of delivering (preventive and/or responsive) stimulation only to the desired regions in the brain. This ensures that the other regions of the brain receive minimal current, while the delivered current is focused on the desired regions (e.g. epileptic foci within the brain). This approach may permit the successful treatment, for example, of brain disorders such as seizures in cases where the use of non-targeting electrodes would not, either because insufficient current is delivered to the desired regions or because of side-effects resulting from the delivery of current to undesired regions of the brain.

In one embodiment of the present invention, the preventive or acute stimulation can be turned on or off manually by the patient or by a another person.

In one embodiment of the present invention, any combination of intracranial positioned electrodes, subpericranial positioned electrodes, subgaleal positioned electrodes, or externally on top of the skin positioned electrodes (skin surface electrodes) can be used simultaneously or sequentially treat a neurological disease.

In one embodiment of the present invention, any combination of intracranial positioned electrodes, subpericranial positioned electrodes, subgaleal positioned electrodes, or electrodes positioned externally on top of the skin can be used simultaneously or sequentially in combination with systemically or localized drug treatment or transcranial magnetic stimulation (TMS) to treat a neurological disease.

Stimulation from subpericranial, subgaleal or skin surface positioned electrodes may cause sensation or pain for the patient.

In one embodiment of the present invention, sensatory nerves of the skull or scalp may be dissected to prevent unpleasant sensation or pain resulting from subpericranial, subgaleal or skin surface positioned electrodes.

In one embodiment of the present invention, subpericranial or subgaleal positioned electrodes are shielded to protect them from electromyographic (EMG) signals. To utilize the shielding the electrodes are isolated on their passive side where they can be covered with foil, plate or grid structured conductors, such as metals.

In one embodiment of the present invention, similar to a noise canceling head phone, EEG signals are sensed via an electrode and these signals are used to create antiphasic correction signals. These correction signals are then sent via the same electrode into the brain to negate or cancel the original EEG signal.

Hybrid Stimulation via Targeting Electrodes

According to one aspect of the present invention, even if both preventive and responsive stimulation is applied to the same patient, the dynamic switching capability provided by the present invention can be employed to apply stimulation to different tissue volumes, statically or dynamically, as may be desired.

The present invention further combines the targeting electrode preventive stimulation approach with an acute responsive stimulation approach to suppress acute epileptic seizure activity of the brain to—what we refer to as—hybrid stimulation via targeting electrodes. In the acute stimulation approach, the EEG activity of the brain is monitored using the targeting electrodes while a seizure detection algorithm detects these EEG signals to determine the onset of seizure activity. Once a seizure is detected stimulation via targeting electrodes starts in order to suppress or stop the epileptic attack.

Low frequency monophasic or biphasic alternating current (AC) may also be used for preventive stimulation. The preventive current may not be provided constantly, but rather in intervals, periodically, aperiodically or episodically. In one embodiment of the present invention, DC, cathodal DC, biphasic or monophasic AC preventive stimulation is delivered from targeting or other electrodes constantly or recurrently in time intervals of constant or changing duration. Preventive DC or AC stimulation may further be provided in episodes, which may contain one or more preventive intervals. Such intervals are typically in the range of from about 10 seconds to about 60 minutes, preferably between 1 minute and 20 minutes. Frequency for preventive AC stimulation is in the range of from about 0.1 Hz to about 100 Hz. When cathodal DC is delivered, the cathode is located in proximity to the seizure focus.

The typical stimulation signals used for acute AC stimulation of the present invention (either preventive or responsive) preferably comprise frequencies in the range of from about 10 Hz to about 250 Hz, although frequencies in the range of from about 0.1 Hz to about 2500 Hz may be effective. The typical width of the acute AC pulse is preferably in the range of from about 50 μsec (microseconds) to about 500 μsec, although pulse widths of about 10 μsec to about 10 sec (seconds) may be effective for a particular patient. The duty cycle, defined as pulse ON time divided by pulse OFF time, can vary from 0.001 to 100. The pulse width of the positive and negative phases may be of different durations and/or magnitudes. Typically, voltage is applied in the range of from about 1 V (volts) to about 100 V, and current amplitudes in the range of from about 5.0 mA (milliamperes) to about 150 mA. Acute stimulation is applied typically for a duration of from about 5 sec to about 30 min (minutes), preferably, from about 10 sec to about 1 min.

As mentioned, direct current stimulation can be employed for a variety of treatments. In order to rehabilitate the electrode surface when using direct current stimulation, it may be desirable in certain instances to employ a reverse bias current, preferably in a manner that has little or no physiologic effect. For example, a reverse bias current can be applied to the electrodes between pulses of DC current to electrolytically remove oxidation/reduction products that may build up on the electrode surfaces over time. It is generally preferred that such reverse bias current have an amplitude sufficiently low to not have any significant physiologic effect but sufficient to prevent electroplating. For example, if a one minute pulse of DC current were applied for one minute every hour, then a reverse bias current $1/59$th of the amplitude of the DC current pulse applied for the remaining 59 minutes of the hour would exactly balance the charge delivered by the DC current pulse and thus rehabilitate the electrode surface without significant physiologic effect.

In one embodiment of the invention, targeting electrodes fixed on top of the scalp are used for testing for a limited period of time to determine if a particular patient and the patient's particular seizure activity is adaptable or treatable with preventive and/or acute stimulation. If such a test is successful, the cutaneous fixed electrodes are then removed and other electrodes are implanted to a subscalp position.

It should be noted here that the preventive stimulation does not have to be performed from targeting electrodes. In one embodiment of the invention, hybrid stimulation performed is a combination of acute stimulation via targeting electrodes and preventive stimulation via non-targeting electrodes. Non targeting electrodes may be any conventional type of electrode, such as disc or stripe type electrode. The electrodes may be located cutaneous, epicranial or intracranial.

System and Method to Treat Epilepsy with Targeting Electrodes

The system for the treatment of epilepsy consists of one or more epicranial located targeting disc-array electrodes, an implanted battery and control unit, implanted leads connecting the battery and control unit with the electrode arrays, and an external programming device capable of communicating via radio frequency with the control unit. The control unit can be implanted anywhere in the body; however, it is preferably implanted on the head under the scalp or in the chest under the collarbones. If implanted under the scalp, the control unit may be fixed to the targeting disc-array electrodes or may be located separately from them.

The epilepsy treatment system of the present invention senses the EEG signals via all or subgroups of electrodes. The epilepsy system comprises a seizure detection and localization algorithm; when a seizure is detected the algorithm will determine the stimulation parameters and electrodes within the array to optimally stimulate the foci and possible foci margins. After each stimulation cycle, the system will sense the EEG signals again and will determine whether to stimulate again and the change in stimulation parameters and electrodes.

In one embodiment of the invention, the epilepsy system is used for EEG recording only. This embodiment seems useful for long term seizure occurrence, seizure intensity and seizure location monitoring.

In one embodiment of the present invention, the stimulation by implanted electrodes is performed in combination with at least one pharmaceutical agent to enhance the therapeutic effect.

In one embodiment of the present invention, sensing and stimulating electrodes may be the same, may be different from each other, or any combination thereof.

In one embodiment of the present invention, sensing, detecting of the seizure focus, and stimulating is performed successively to follow a moving or in time and space varying seizure focus.

In one embodiment of the present invention, the cutaneous electrodes stimulate jointly utilizing a phased array method.

In one embodiment of the present invention, the epicranial implanted electrodes stimulate jointly utilizing a phased array method.

In one embodiment of the invention, the discrete-arrays are implanted in or on top of the brain, and have direct contact with brain tissue.

The typical stimulation signals used in the implantable device of the present invention are preferably biphasic (that is, with equal energy positive and negative of ground), with a typical frequency in the range of from about 1 Hz to about 500 Hz, preferably, from about 10 Hz to about 250 Hz, although frequencies in the range of from about 0.1 Hz to about 2500 Hz may be effective. The typical width of the biphasic pulse is preferably between about 50 μsec (microseconds) and about 500 μsec, although pulse widths of about 10 μsec to about 10 sec (seconds) may be effective for a particular patient. The pulse width of the positive and negative phases may be of different durations and/or magnitudes. Typically, voltages in the range of from about 10 mV to about 200 V may be suitable for use herein, preferably from 10 mV (milli volts) to about 100 V (volts), more preferably from about 100 mV to about 20 V, and current amplitudes in the range of from about 5.0 mA (milli amperes) to about 50 mA, although current amplitudes in the range of about 0.01 mA to about 1000 mA maybe suitable for use herein. However, it may be beneficial using magnitudes above 2000 V if the skin-to-electrode impedance is above 40,000 ohms. Stimulation is applied for a duration of from about 15 sec to 30 min (minutes), preferably, from about 30 sec to about 5 min.

In one embodiment of the invention, the discrete electrodes, from which the discrete-arrays are constructed, are round discs with diameters typically from about 1 to about 10 mm. Concentric ring electrodes having 1 center disc and 1 to 10 rings are useful herein, however, 1 to 3 rings are typically used. Generally, the rings are of equal radial distance from each other, but can also be of varying radial distance. The radial distance is between 0.3 mm and 30 mm, preferably, between 3 mm and 10 mm. The rings in general are of equal width, but can also be of varying width. The width of the rings is between 0.1 mm and 10 mm, preferably, between 1 mm to 3 mm. The center disc electrode has a radius of up to 10 mm, preferably, between 2 mm and 4 mm. Some ring electrodes may not have a center disc electrode. In general, ring electrodes are concentric, but they may also be elliptical. The ratio of the two elliptic axes is up to 10, preferably up to 2. The thicknesses of the electrodes in a ring electrode are typically about equal, but they can also vary. Typically, electrode thicknesses are between 0.001 mm and 0.01 mm, but they can range between 0.0001 mm and 1.0 mm. The electrodes are preferably fabricated from a metal, such as gold, stainless steel, platinum, copper, copper alloys, titanium, or titanium alloys.

The number of targeting electrodes in a typical implantable device is typically between 1 and 12, but can also be between 1 and 100. Any neurological disorder can be treated with the device of the present invention. The present device can also be used purely for sensing, such as EEG. The device can be implanted temporarily or permanently, and it can be implanted intracranial.

The device of the present invention comprises a detection algorithm that detects seizures from the sensed signals. For moderate starting seizure signals, moderate stimulation is administered. If the seizure evolves, more intense stimulation is administered, which comprises more pulses or more amplitude or a combination of both. If the detected seizure signals decrease, then less stimulation is administered.

Determining the correct location for positioning the electrodes can be accomplished using Magnetic Resonance Imaging (MRI), functional MRI (fMRI), Diffusion Weighted MRI (DWI), Diffusion Tensor MRI (DTI), x-ray fluoroscopy, Computer Tomography (CT), Ultrasound (US), Single Photon Emission Computed Tomography (SPECT), or Positron Emission Tomography (PET).

In one embodiment of the present invention, targeting disc-array electrodes or solid ring electrodes are taped, clamped, stapled or otherwise fixed onto the skin in the form of a plaster.

In one embodiment of the invention, targeting electrodes fixed on top of the scalp are used to test for a limited period of time to determine if a particular patient and the patient's particular neurological disorder is adaptable or treatable with stimulation. If such a test is successful, the fixed electrodes are then removed and other electrodes are implanted sub-scalp.

As noted above, the present invention is applicable to devices and methods for the electrical stimulation treatment of neurological disorders. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

Rehabilitation of Electrodes

When the electrical current delivered through an electrode which is in contact with tissue does not have a mean value of zero when averaged over time, ionic compounds in the tissue may deposit on the electrode. These deposits will alter the electrical conductive properties of the electrode and may also result in potential differences between the electrode and the tissue with which the electrode is in contact. This situation would occur, for example, if DC current stimulation is used. One embodiment of the present invention, prevents the undesirable accumulations when periodic stimulation is performed to alter brain electrical activity. In this embodiment, during the intervals, between the intervals when the desired stimulation current is delivered through the electrode, a "reverse" current is delivered through the electrode which has an integrated over time value approximately of equal magnitude but opposite in sign to the integrated over time value of the current during the stimulation intervals. The integrated over time value of a current is the total electrical charge delivered. Thus in the method of this invention, the net electrical charge over time delivered through the electrode is approximately zero. As a result the accumulations on the electrode are greatly reduced or eliminated. Furthermore, if the intervals between the stimulation intervals are much longer in duration than the stimulation intervals, then the mean magnitude of the reverse current will be much smaller than the mean magnitude of the stimulation current. If the mean magnitude of the reverse current is sufficiently small it may have little or no physiologic effect with regard to brain electrical activity, but will prevent the electroplating that would otherwise have occurred. For example, suppose an electrode is used to deliver one milliampere of DC anodal current for one minute out of every hour of the day to prevent seizure activity. In the method of this invention, a reverse DC anodal current of magnitude 1/59 of one milliampere could be delivered during the 59 minute periods between stimulations. This reverse current in this case would be so small as to result in little or no physiologic effect in terms of brain electrical activity, but would rehabilitate the electrode.

Low Frequency Stimulation

All stimulation attempts known to treat epilepsy in humans via AC stimulation have used stimulation frequencies greater than 20 Hz. One study (Hallett et.al., "Transcranial magnetic stimulation and the human brain," Nature, Vol. 406, 13 Jul. 2000) states that while "rapid repetitive transcranial magnetic stimulation (rTMS), at frequencies of 5 Hz and higher, will transiently enhance motor excitability . . . slow rTMS, at 1 Hz will transiently depress excitability." Paatta et al. ("Control of chronic experimental focal epilepsy by feedback caudatum stimulation," Epilepsia 1983 August; 24(4): 444-54) describe successful ictal spike depression by 5 Hz stimulation of the caudate nucleus (CN) in cat brains.

In one embodiment of the present invention, the stimulation frequency for preventive or acute stimulation as provided from subpericranial, subgaleal or skin surface positioned electrodes is in the range of about 0.1 Hz and about 10 Hz.

Pericranial Electrodes

In contrast to intracranial implanted electrodes as described in U.S. Pat. No. 5,938,689, US 2005/0,154,435 or U.S. Pat. No. 5,792,186 subpericranial, subgaleal or skin surface positioned electrodes allow a more flexible reaction to seizures. Seizure foci of the brain may shift in their location and size over time and during a seizure. Intracranial implanted electrodes are fixed in their location; while subpericranial, subgaleal or skin positioned electrodes, especially when utilized as Laplace electrodes, are capable to not only stimulate the focus but also a varying margin around the focus. Subpericranial, subgaleal or skin positioned Laplace electrodes may be constructed by virtually connecting single disc-like electrodes, which may be implanted as an array (10×10 or 20×30, etc.), and thus the technology allows to virtually define any type of locally fixed or moving electrode. Due to their locally fixed nature, stimulation technologies using intracranial electrodes are applied to the same patient populations which are candidates for brain surgery. Thus while these technologies compete with brain surgery, technologies using more flexible and systemic alike stimulation schemes from targeted electrodes tends to compete with drugs, since stimulation is not known to have the devastating side effects that drugs.

Figure 12:
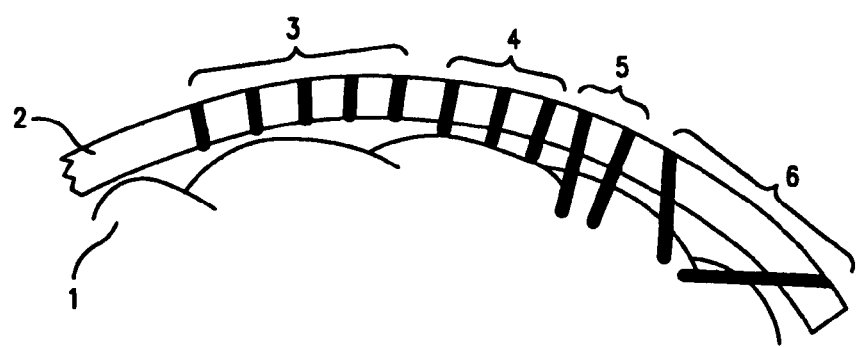
FIG. 12 schematically illustrates a cross-section of an electrode array.

However, if it is desired to position the electrodes in more proximal distance to brain structures, pericranial electrodes as shown in FIG. 12 can be used. FIG. 12 illustrates a cross sectional view of a portion of the brain 1 and the skull 2. Scalp structures are not shown.

In one embodiment of the present invention, an array of tiny holes is drilled through the cranium to insert an array of pin type electrodes. After inserting these pericranial electrodes, the holes are sealed against bacteria or other infectious tissue, using silicon materials or other means.

In one embodiment of the present invention, the pericranial electrodes are building an equally spaced array with constant distances between the electrodes.

In one embodiment of the present invention, the pericranial electrodes are building an unequally spaced array with varying distances between the electrodes. In one embodiment of the present invention, the electrodes are used for sensing EEG signal and for stimulation.

In one embodiment of the present invention, the electrodes are electrically connected in such a way, that they build a virtual Laplace electrode or any other type of targeted electrode.

In one embodiment of the present invention, the brain facing ends of the pericranial electrodes 3 do not touch the brain.

In one embodiment of the present invention, the brain facing ends of the pericranial electrodes 4 do touch the brain or the dura mater.

In one embodiment of the present invention, the brain facing ends of the pericranial electrodes 5 penetrate into the brain.

In one embodiment of the present invention, the pericranial electrodes 6 do not penetrate the cranium orthogonal.

Radio Controlled Data Exchange

In one embodiment of the present invention, the electrodes, leads and power supply, which can be battery pack and a control unit, are implanted, and the stimulation instructions are sent via radio signals to the control unit. The stimulation instructions provide the implanted system with information from which electrodes with which stimulation parameters (current, voltage, duty cycle, frequency) stimulation is to be performed.

As noted above, the present invention pertains to medical devices for the treatment of neurological and nervous disorders via electrical stimulation, and methods related thereto. The present invention should not be considered limited to the particular embodiments described above, but rather should be understood to cover all aspects of the invention as fairly set out in the appended claims. Various modifications, equivalent processes, as well as numerous structures to which the present invention may be applicable will be readily apparent to those skilled in the art to which the present invention is directed upon review of the present specification. The claims are intended to cover such modifications.

We claim:

1. A system for treatment of neurological disorders in a patient, comprising:
   a plurality of electrodes configured to be arranged in an array adapted for placement outside a skull of the patient to deliver electrical stimulation to the patient's brain, wherein said electrodes are discrete disc-type electrodes;
   a power supply; and
   a control module operatively coupled to the power supply and including a switching sub-system operatively coupling the control module to the plurality of electrodes;
   wherein the switching sub-system selects electrodes individually among the plurality of discrete disc-type electrodes to administer electrical stimulation so as to switch selected electrodes between electrical phasing patterns without altering the placement of the plurality of electrodes, and
   wherein the switching sub-system is further configured to deliver electrical stimulation by individually adjusting an amplitude and sign of the electrical stimulation delivered through each of the plurality of discrete disc-type electrodes to achieve an electrical phasing pattern of a laplacian or concentric electrode, and permit targeting of a predetermined volume of brain tissue.

2. The system according to claim 1, wherein the control module further comprises an analysis sub-system to analyze electrical activity sensed by the selected electrodes.

3. The system according to claim 2 wherein the control module further includes a targeting sub-system for targeting electrical stimulation for delivery into a selected area of the brain.

4. The system according to claim 3 wherein the switching sub-system responds to the targeting sub-system to deliver targeted electrical stimulation into a selected area of the brain.

5. The system according to claim 1 wherein the control module further comprises a localizing sub-system to localize a source of the electrical activity.

6. A method for treating neurological disorders in a patient, comprising the steps of:
(a) positioning a plurality of electrodes arranged in an array, outside the patient's skull, wherein said electrodes are discrete disc-type electrodes;
(b) providing a power supply;
(c) operatively coupling a control module to the power supply;
(d) coupling the control module to the plurality of electrodes through a switching subsystem;
(e) selecting electrodes among the plurality of electrodes with the switching subsystem; and
(f) delivering an electric stimulation into a predetermined volume of the brain of the patient through the selected electrodes by switching the selected electrodes individually among the plurality of electrodes with the switching sub-system between preselected electrical phasing patterns without altering the placement of the plurality of electrodes, wherein an amplitude and sign of the electrical stimulation delivered through each of the plurality of discrete disc-type electrodes are individually adjusted by the switching sub-system to achieve an electrical phasing pattern of a laplacian or concentric electrode.

7. The method according to claim 6 further comprising the step of localizing a source of electrical activity within the brain of the patient.

8. The method according to claim 7 further comprising the step of targeting stimulation for delivery to the patient's brain adjacent the source of the electrical activity.

9. The method according to claim 8 further comprising the step of delivering targeted electrical stimulation into a selected area of the patient's brain.

10. The method of claim 6, wherein the electrical stimulation is a direct current stimulation.

11. The method of claim 6, wherein the electrical stimulation is a low frequency stimulation.

12. The method of claim 11, wherein the low frequency stimulation is less than 20 Hz.

13. The method of claim 6, wherein the electrical stimulation is greater than 15 seconds.

14. The method of claim 13, wherein the electrical stimulation is a direct current stimulation or an alternating current stimulation.

* * * * *